(12) United States Patent
Jefferies et al.

(10) Patent No.: US 10,792,347 B2
(45) Date of Patent: Oct. 6, 2020

(54) METHODS FOR DIAGNOSING AND TREATING ALZHEIMER'S DISEASE

(71) Applicants: Wilfred Jefferies, Surrey (CA); Kaan E. Biron, North Vancouver (CA); Dara L. Dickstein, New York, NY (US)

(72) Inventors: Wilfred Jefferies, Surrey (CA); Kaan E. Biron, North Vancouver (CA); Dara L. Dickstein, New York, NY (US)

(73) Assignee: Alternative Extracts Inc., Vancouver (CA)

( * ) Notice: Subject to any disclaimer, the term of this patent is extended or adjusted under 35 U.S.C. 154(b) by 0 days.

(21) Appl. No.: 15/496,106

(22) Filed: Apr. 25, 2017

(65) Prior Publication Data

US 2017/0224792 A1    Aug. 10, 2017

Related U.S. Application Data

(63) Continuation of application No. 14/233,606, filed as application No. PCT/CA2012/050488 on Jul. 18, 2012.

(Continued)

(51) Int. Cl.
*A61K 47/68* (2017.01)
*A61K 47/64* (2017.01)
(Continued)

(52) U.S. Cl.
CPC .......... *A61K 39/0007* (2013.01); *A61K 31/05* (2013.01); *A61K 31/192* (2013.01); *A61K 31/404* (2013.01); *A61K 31/42* (2013.01); *A61K 31/436* (2013.01); *A61K 31/44* (2013.01); *A61K 31/506* (2013.01); *A61K 31/551* (2013.01); *A61K 38/1709* (2013.01); *A61K 38/195* (2013.01); *A61K 38/208* (2013.01);
(Continued)

(58) Field of Classification Search
None
See application file for complete search history.

(56) References Cited

U.S. PATENT DOCUMENTS

2004/0202651 A1* 10/2004 Cohen .............. A61K 39/39541
                                                    424/131.1
2007/0196375 A1    8/2007 Tobinick
2010/0144790 A1    6/2010 Shen et al.

FOREIGN PATENT DOCUMENTS

WO    2009155504 A2    12/2009
WO    2010059541 A1    5/2010
WO    2011006157 A2    1/2011

OTHER PUBLICATIONS

Avery et al. Intravitreal Bevacizumab (Avastin) in the Treatment of Proliferative Diabetic Retinopathy.Ophthalmology vol. 113, Issue 10 (Oct. 2006) 1695-1705 (Year: 2006).*

(Continued)

*Primary Examiner* — Aurora M Fontainhas
(74) *Attorney, Agent, or Firm* — Wood Herron & Evans LLP

(57) ABSTRACT

Methods for diagnosing and treating Alzheimer's disease are provided. In particular, methods of restoring blood-brain barrier integrity and/or promoting vascular reversion in a person suffering from Alzheimer's disease by administering an anti-angiogenic agent or an agent that is capable of restoring tight junction integrity. Methods of preventing or delaying the onset of Alzheimer's disease in a subject are also provided.

5 Claims, 20 Drawing Sheets

Related U.S. Application Data

(60) Provisional application No. 61/687,071, filed on Apr. 18, 2012, provisional application No. 61/509,538, filed on Jul. 19, 2011.

(51) Int. Cl.

| | |
|---|---|
| *A61P 25/00* | (2006.01) |
| *A61P 25/28* | (2006.01) |
| *A61K 39/00* | (2006.01) |
| *A61K 38/20* | (2006.01) |
| *A61K 31/506* | (2006.01) |
| *A61K 38/19* | (2006.01) |
| *A61K 38/21* | (2006.01) |
| *A61K 38/48* | (2006.01) |
| *A61K 31/42* | (2006.01) |
| *A61K 31/192* | (2006.01) |
| *A61K 31/551* | (2006.01) |
| *A61K 38/39* | (2006.01) |
| *A61K 31/404* | (2006.01) |
| *A61K 31/44* | (2006.01) |
| *A61K 31/05* | (2006.01) |
| *A61K 31/436* | (2006.01) |
| *A61K 38/17* | (2006.01) |
| *C07K 16/18* | (2006.01) |
| *C07K 16/22* | (2006.01) |
| *G01N 33/50* | (2006.01) |

(52) U.S. Cl.
CPC ............ *A61K 38/21* (2013.01); *A61K 38/212* (2013.01); *A61K 38/39* (2013.01); *A61K 38/484* (2013.01); *C07K 16/18* (2013.01); *C07K 16/22* (2013.01); *G01N 33/5058* (2013.01); *A61K 2039/55566* (2013.01); *A61K 2039/575* (2013.01)

(56) References Cited

OTHER PUBLICATIONS

Wu, Han-Chung, "Anti-Angiogenic Therapeutic Drugs for Treatment of Human Cancer," Journal of Cancer Molecules, vol. 4, No. 2, pp. 37-45, ISSN 1817-4256 (Jun. 17, 2008) (9 pages).

Canadian Intellectual Property Office, International Search Report issued in corresponding International Patent Application No. PCT/CA2012/050488 dated Oct. 10, 2012 (5 pages).

State Intellectual Property Office of the People's Republic, Notification of the First Office Action issued in corresponding Chinese Patent Application No. 201280045676.1 and English-language translation dated Dec. 5, 2014.

European Patent Office, Extended European Search Report issued in corresponding European Patent Application No. 12814751.9 dated May 7, 2015.

State Intellectual Property Office of the People's Republic, Notification of the Second Office Action issued in corresponding Chinese Patent Application No. 201280045676.1 and English-language translation dated Aug. 27, 2015.

Dickstein, Dara L, et al., "Aß Peptide Immunization Restores Blood-Brain Barrier Integrity in Alzheimer Disease," FASEB J. vol. 20, No. 3, pp. 426-433 (Mar. 1, 2006).

Ryu, Jae K. et al., Thalidomide Inhibition of Perturbed Vasculature and Glial-Derived Tumor Necrosis Factor-a in an Animal Model of Inflamed Alzheimer's Disease Brain. Neurobiology of Disease, Blackwell Scientific Publications, Oxford, GB, vol. 29, No. 2, pp. 254-266 (Jan. 15, 2008).

Cramer, Paige E., et al., "ApoE-Directed Therapeutics Rapidly Clear β-Amyloid and Reverse Deficits in AD Mouse Models," Science, vol. 335, No. 6075, pp. 1503-1506 (Mar. 23, 2012).

Citron. Alzheimer's Disease: Strategies for Disease Modification. Nat Rev Drug Discov. May 2010; 9(5):387-98.

Chinese Patent Office, Office Action issued in Chinese Patent Application No. 201610034613.6 dated Jan. 9, 2018, 8 pages.

Ji and Ha. "Drug Development for Alzheimer's Disease: Recent Progress," Exp Neurobio. 2010; 19:120-131.

Australian Patent Office, Examination Report issued in Australian Patent Application No. 2017203339 dated Feb. 8, 2018, 5 pages.

\* cited by examiner

Figure 1: Tg2576 AD mice have cerebral tight junction pathology.

Figure 2
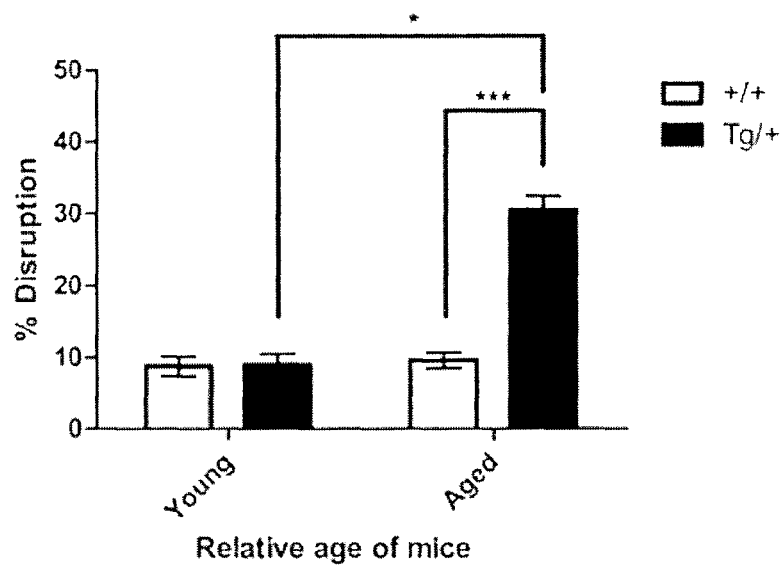
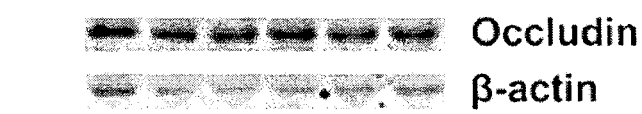
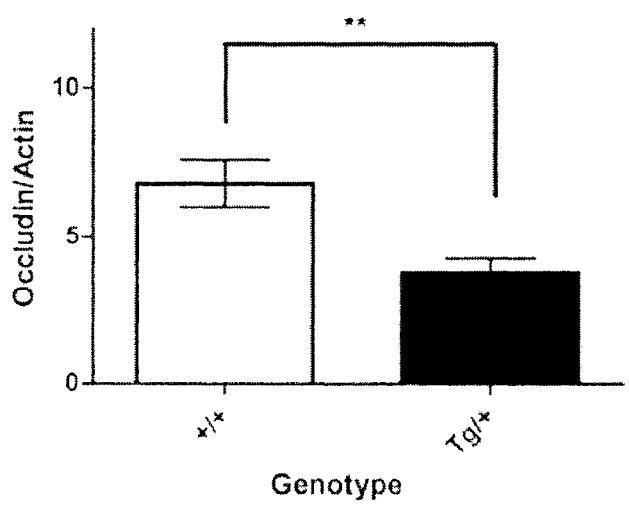

Figure 2 continued
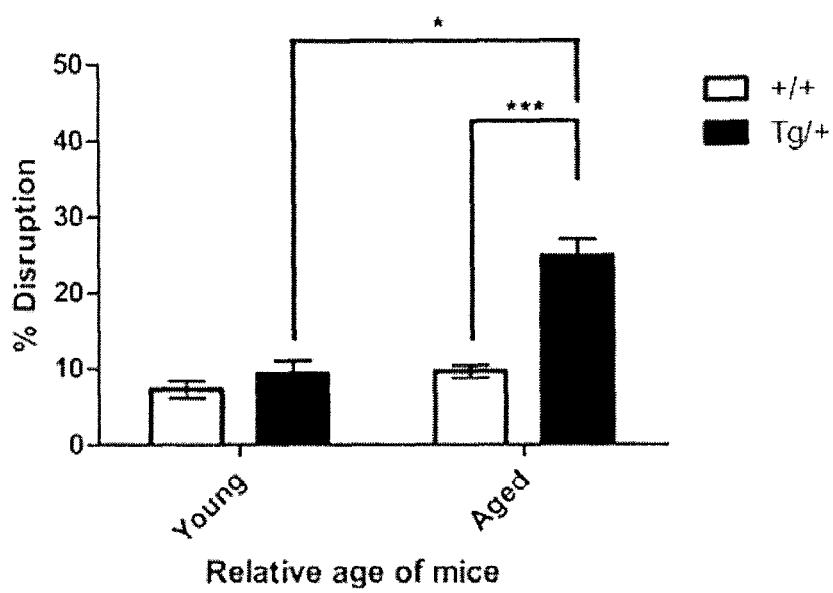
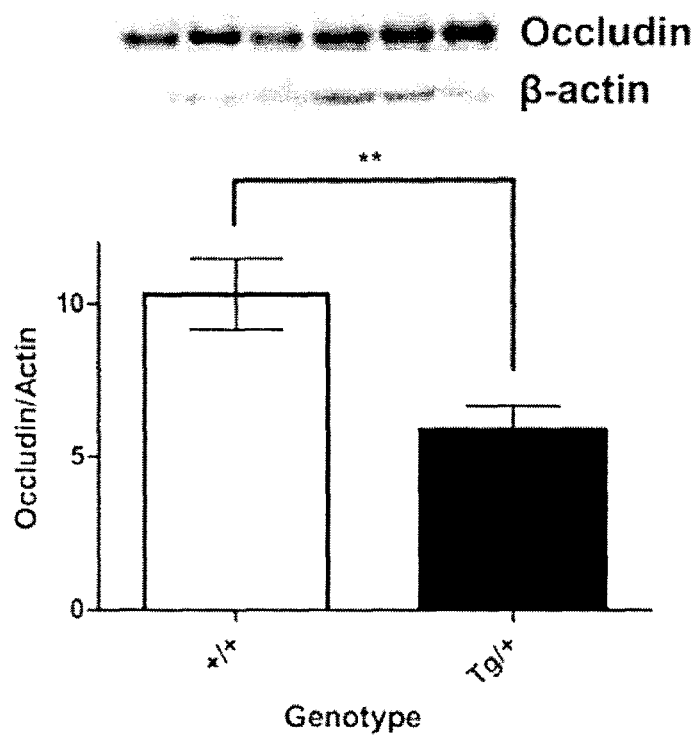

Figure 3: Angiogenesis not apoptosis induces alterations in tight junction immunoreactivity.

Figure 4
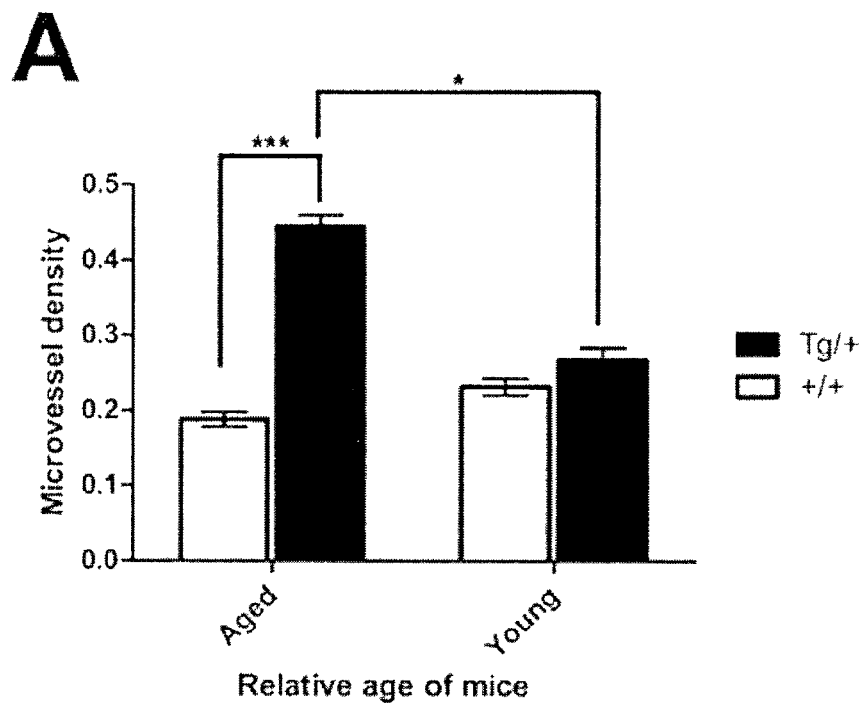
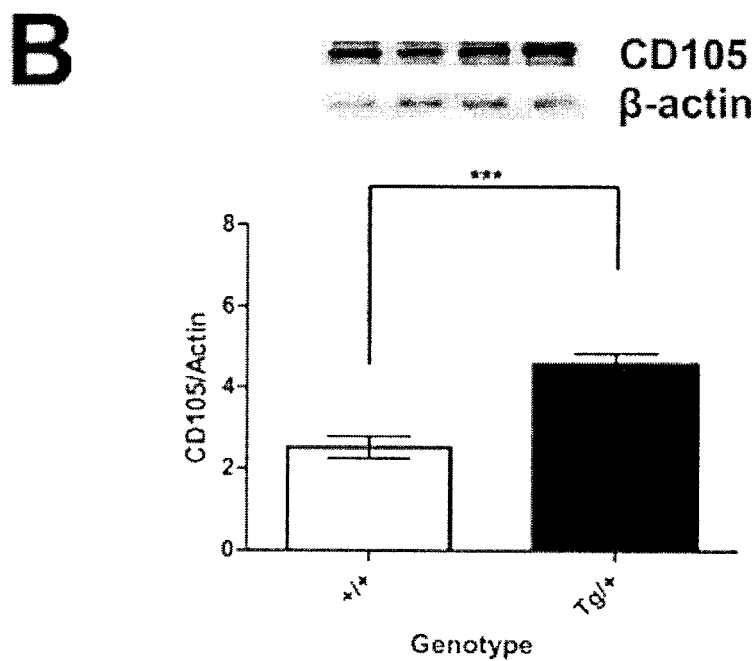

Figure 4 continued
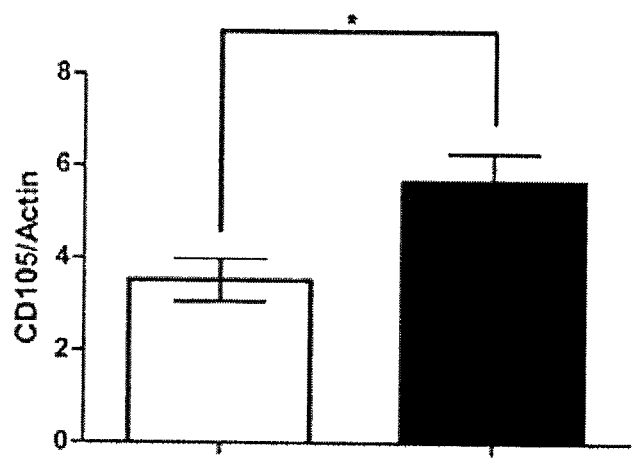
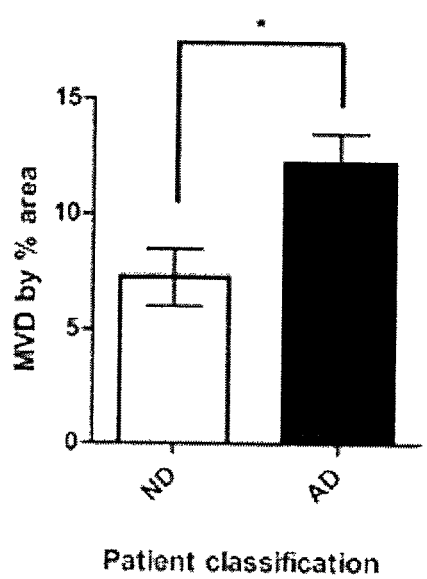
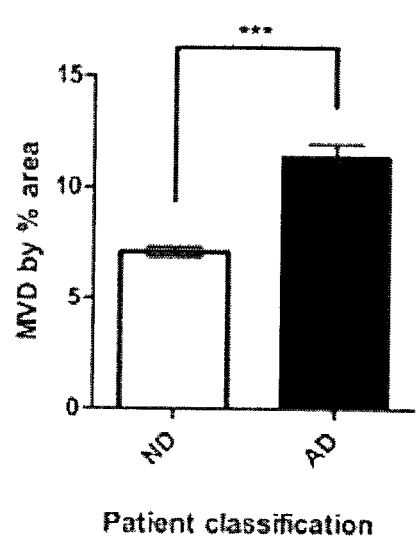

Figure 4 continued
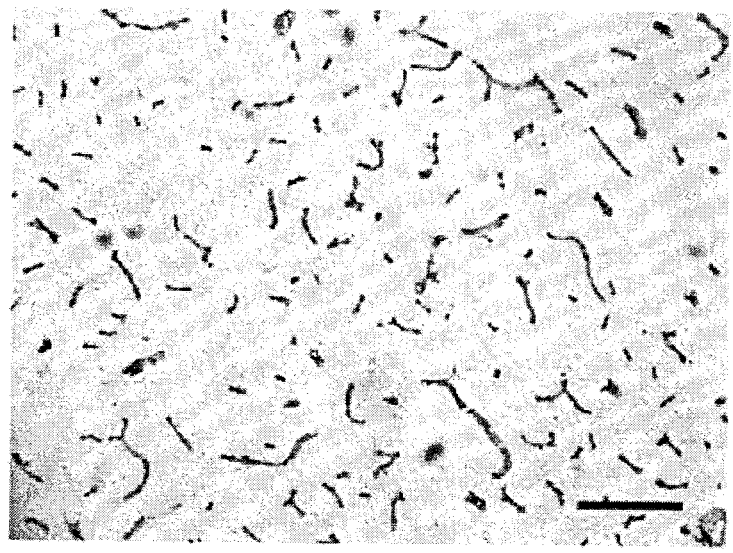
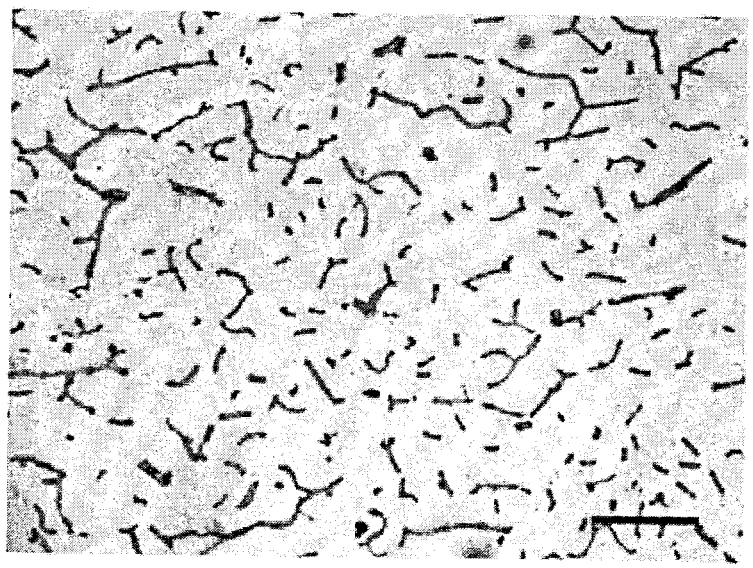

Figure 13 continued
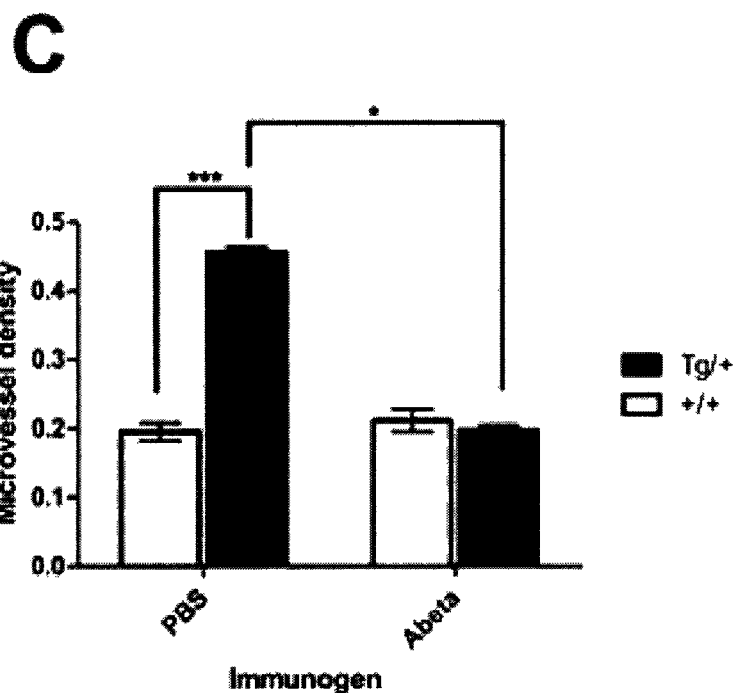
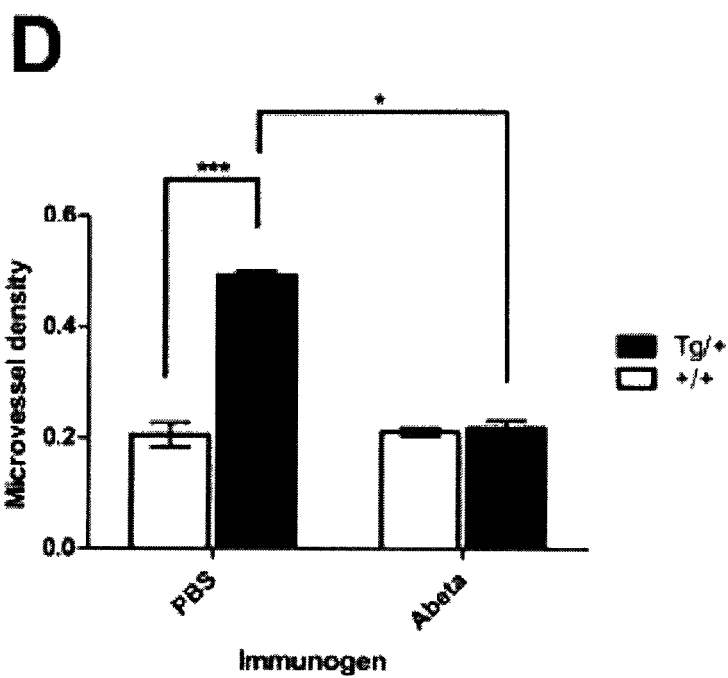

Figure 13 continued
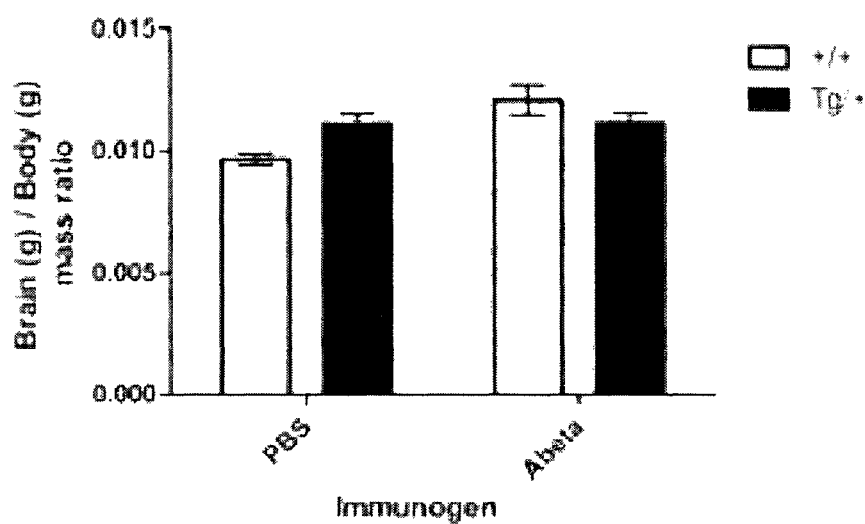
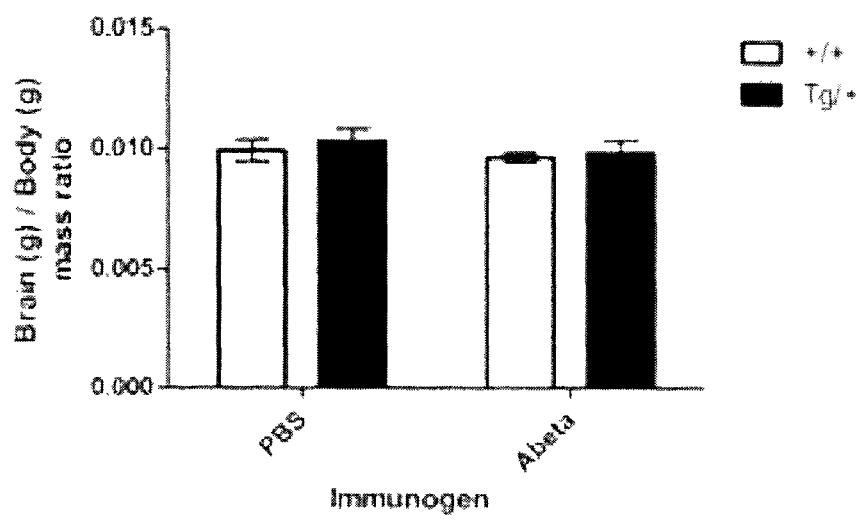

METHODS FOR DIAGNOSING AND TREATING ALZHEIMER'S DISEASE

FIELD OF THE INVENTION

The present invention relates to the field of diagnostics and therapeutics, in particular as they relate to Alzheimer's disease.

BACKGROUND OF THE INVENTION

Alzheimer's disease is the most common form of dementia. The cause and progression of the disease are not well understood, but the progressive formation of amyloid plaques and vascular deposits of amyloid beta-peptide have long been considered the pathological hallmark of Alzheimer's disease.

Blood brain barrier (BBB) dysfunction was initially identified in animal models of Alzheimer's disease and precedes the formation of senile plaques in these animal models (Ujiie, et al., (2003), *Microcirculation,* 10: 463-470). BBB dysfunction was later confirmed as a prominent, though unexplained, clinical feature of Alzheimer's disease in patients (Farrall & Wardlaw, (2009) *Neurobiol Aging* 30: 337-352). The origin of BBB dysfunction during Alzheimer's disease is not known, but amyloid-beta peptide (abeta) may be directly involved in this process as BBB leakiness has been demonstrated in a number of Alzheimer's disease transgenic animals models in which forms of amyloid precursor protein (APP) are overexpressed (Ujiie, et al., ibid.; Kumar-Singh, et al. (2005) Am J Pathol 167: 527-543; Paul, et al., (2007) J Exp Med 204: 1999-2008; Dickstein, et al. (2006) Faseb J, 20: 426-433). Vaccination with abeta peptide has been shown to reverse BBB pathology (Dickstein, et al., ibid.).

Anderson, et al. (Cardiovascular Psychiatry and Neurology, (2011), Article ID 616829) proposed that water regulation is disturbed in Alzheimer's disease and results in abnormal permeability of the BBB and abnormal rates of exchange across the vessel walls.

A high incidence of microangiopathy in Alzheimer's disease has been reported (Perlmutter, et al., (1990), Brain Res. 508(1):13-19). Ongoing angiogenesis in brain regions affected by Alzheimer's disease has also been reported and has been suggested to the related to tissue injury (Desai, et al., (2009), J Neural Transmission, 116(5):587-597).

Chronic use of certain drugs, such as non-steroidal anti-inflammatories, lipid lowering statins, histamine H2 receptor blockers and calcium channel blockers have been reported to decrease the risk of Alzheimer's disease in high-risk populations. These agents may also have anti-angiogenic properties leading to a preliminary hypothesis that Alzheimer's disease is mediated by pathological angiogenesis and that angiogenic activation of the brain endothelium leads to deposition of beta amyloid plaques and secretion of a neurotoxic peptide that kills critical neurons (Vagnucci & Li, (2003), Lancet, 361:605-608).

Methods of inhibiting angiogenesis employing an anti-angiogenic agent selected from a p190RhoGAP activator, a TFII-I activator, a GATA-2 inhibitor in an angiogenesis-related disease or disorder characterized by increased angiogenesis, such as, macular degeneration; diabetic retinopathy; rheumatoid arthritis; Alzheimer's disease; obesity; psoriasis; atherosclerosis; vascular malformations; angiomata; and endometriosis have been previously described (WO 2009/155504).

This background information is provided for the purpose of making known information believed by the applicant to be of possible relevance to the present invention. No admission is necessarily intended, nor should be construed, that any of the preceding information constitutes prior art against the present invention.

SUMMARY OF THE INVENTION

An object of the present invention is to provide methods of diagnosing and treating Alzheimer's disease.

In accordance with an aspect of the present invention, there is provided a method of treating or delaying onset of Alzheimer's disease by inhibiting angiogenesis in the brain of individual's having or at risk of Alzheimer's disease.

In accordance with another aspect of the present invention, there is provided a method of treating Alzheimer's disease by administering an anti-angiogenic agent alone or in combination with a therapeutic agent.

In accordance with an aspect of the present invention, there is provided a method of restoring blood-brain barrier (BBB) integrity in a subject having or at risk of developing Alzheimer's disease comprising administering to the subject an effective amount of an anti-angiogenic agent and/or an agent that prevents abeta amyloidogenesis and/or promotes removal of abeta peptide from the brain.

In accordance with an aspect of the present invention, there is provided a method of maintaining blood-brain barrier integrity in a subject comprising administering to the subject an effective amount of an anti-angiogenic agent and/or an agent that that inhibits abeta amyloidogenesis and/or promotes removal of abeta peptide from the brain.

In accordance with another aspect of the invention, there is provided a method of promoting vascular reversion in the brain of a subject having or at risk of developing Alzheimer's disease comprising administering to the subject an effective amount of an anti-angiogenic agent and/or an agent that promotes the removal of abeta peptide from the brain.

In accordance with another aspect of the invention, there is provided a method of preventing or delaying blood-brain barrier leakiness in a subject comprising administering the subject an effective amount of an anti-angiogenic agent and/or an agent that inhibit abeta amyloidogenesis and/or promotes removal of abeta peptide from the brain.

In accordance with another aspect of the invention, there is provided a method for identifying subjects at risk of developing Alzheimer's disease, or having early stage Alzheimer's disease, comprising detecting angiogenesis, TJ disruption and/or blood-brain barrier disruption in the brain of a subject.

In accordance with another aspect of the invention, there is provided a method of identifying potential therapeutic agents for the treatment of Alzheimer's disease comprising testing the ability of a candidate agent to restore tight junctions in cerebral blood vessels or to promote vascular reversion in the brain.

BRIEF DESCRIPTION OF THE DRAWINGS

These and other features of the invention will become more apparent in the following detailed description in which reference is made to the appended drawings.

FIG. 2: Aged Tg2576 Mice have reduced tight function expression. The expression of occludin or ZO-1 were compared quantitatively between wild-type and Tg2576 mice in the neocortex (A and B) and hippocampus (C and D). (A) The percentage of cortical cerebral blood vessels with abnormal ZO-1 expression patterns was significantly higher in the aged Tg2576 mice compared to age-matched wild-type (***p<0.001). The incidence of ZO-1 disruption was also significantly higher in aged Tg2576 mice compared to young Tg2576 (Young wild-type, n=4; Young Tg2576, n=3; aged wild-type, n=5; aged Tg2576, n=4; *p<0.05) in the cortex. (B) Aged Tg2576 mice had significantly reduced occludin protein levels in the cortex compared to age-matched wild-type (n=7, p=0.0072). (C) The percentage of hippocampal cerebral blood vessels with abnormal ZO-1 expression patterns was significantly higher in the aged Tg2576 mice compared to age-matched wild-type (*p<0.001). Similarly, the incidence of ZO-1 disruption was also significantly higher in aged Tg2576 mice compared to young Tg2576 (Young wild-type, n=4; Young Tg2576, n=3; aged wild-type, n=5; aged Tg2576, n=4; *p<0.05) in the hippocampus. (D) Aged Tg2576 mice had significantly reduced occludin protein levels in the hippocampus compared to age-matched wild-type (n=7, **p=0.0076). Values represent mean±SEM.

FIG. 4: Microvascular Density is increased in Aged Tg2576 and in Human patients with AD. The MVD, by CD105 staining, in the cerebrovasculature and CD105 protein expression were quantified in aged and young Tg2576 and wild-type. (A) Aged Tg2576 mice had a significantly higher MVD compared to age-matched wild-type (***p<0.001). Aged Tg2576 were had a significantly higher MVD compared to young Tg2576 (Aged wild-type, n=5; aged Tg2576, n=4; young wild-type, n=4; young Tg2576, n=3; *p<0.05). Although not significant, young Tg2576 mice trended to a higher average MVD compared to wild-type. (B) Aged Tg2576 mice had a significantly increased CD105 protein levels in the cortex compared to age-matched wild-type (wild-type, n=5; Tg2576, n=6; ***p<0.001). (C) Aged Tg2576 mice had a significantly increased CD105 protein levels in the hippocampus compared to age-matched wild-type (n=7, *p<0.05). (D) The cortex of the AD patient had a significantly increased MVD, as measured by % area occupied by laminin staining, compared to the ND patient (n=4, *p<0.05). (E) The hippocampus of the AD patient had a significantly increased MVD, as measured by % area occupied by laminin staining, compared to the ND patient (n=4, ***p<0.001). Representative images of immunohistochemical staining for laminin in the cortex of the ND patient (F) and the AD patient (G). Scale bar represents 95 μm. Values represent mean±SEM.

DETAILED DESCRIPTION OF THE INVENTION

Figure 1:
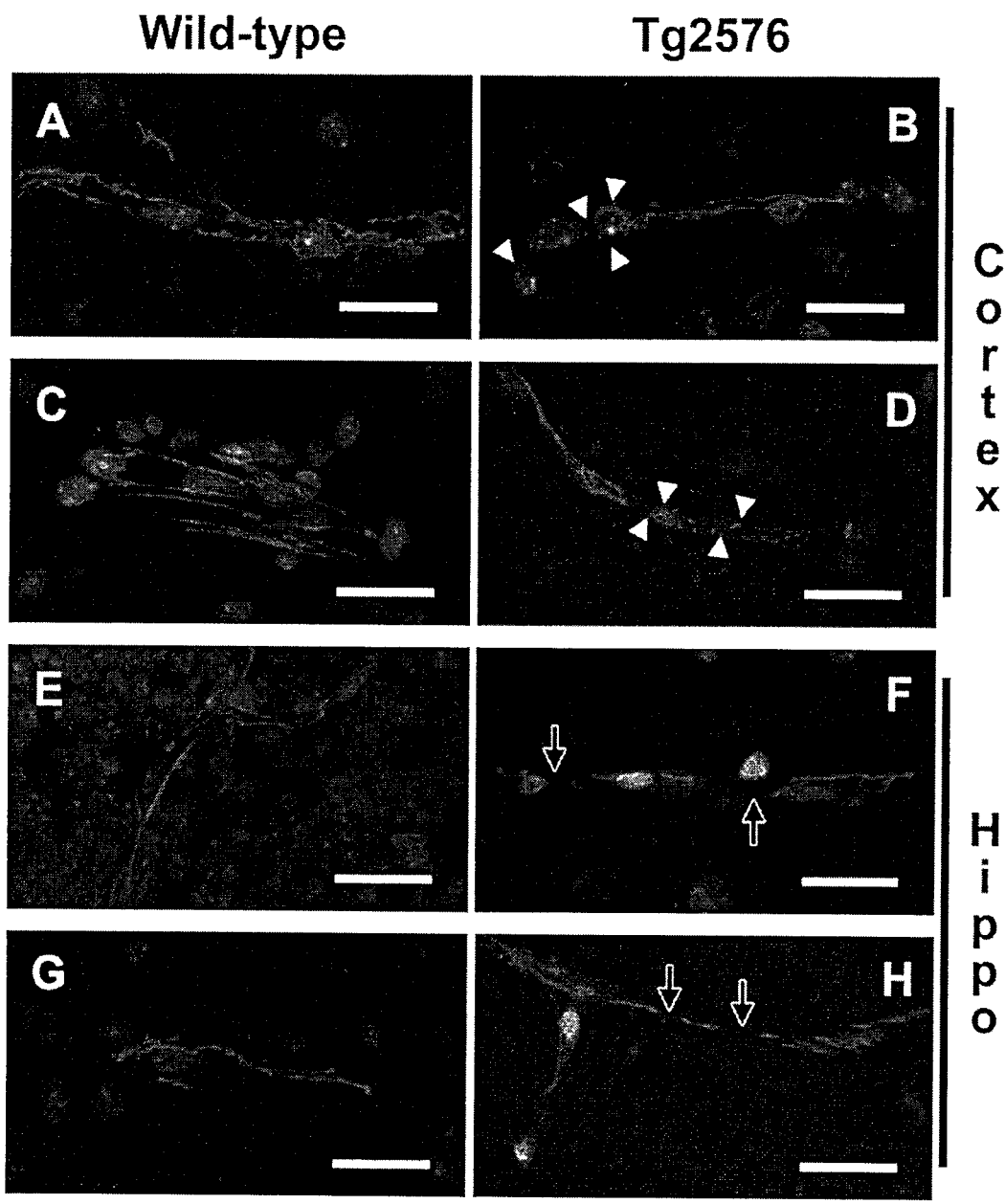
FIG. 1: Tg2576 AD mice have cerebral tight junction pathology. This figure presents representative confocal micrographs of cerebral blood vessels from aged Tg2576 and wild-type mice immunolabeled for either occludin or ZO-1 (red) and counterstained for DNA (blue) with TOTO- 3. Blood vessels, imaged in the neocortex and hippocampus, which exhibited strong, continuous and linear occludin (A and C) or ZO-1 (E and G) expression were considered normal, as demonstrated in the wild-type. Abnormal occludin (B and F) and ZO-1 (D and H) staining displayed punctate (white arrowheads), discontinuous or interrupted (hollow white arrows), as seen in the Tg2576 cerebrovasculature. Results are representative from three mice per group from three separate experiments. Scale bar represents 20 μm.

Reduced BBB integrity precedes other Alzheimer's disease pathologies such as amyloid plaques and therefore maintaining or reestablishing the integrity of the BBB may be useful in the treatment and/or prevention of Alzheimer's disease. The present invention relates to the finding, described herein, that this reduced BBB integrity is due to angiogenesis in the brain. In particular, angiogenesis in the brain results in the disruption of tight junctions that maintain the BBB. Inhibition of angiogenesis allows restoration of the tight junctions, which will in turn decrease the "leakiness" of the BBB. In addition, vaccination with abeta peptide has been shown to result in vascular reversion and restoration of tight junctions.

Accordingly, in certain embodiments, there is provided a method of treating and/or delaying the onset of Alzheimer's disease pathologies by inhibiting angiogenesis in the brain. In certain embodiments, the invention provides for methods of maintaining and/or restoring BBB integrity in a person by inhibiting angiogenesis in the brain and/or restoring tight junctions in cerebral vessels. In certain embodiments, these methods comprise administering one or more anti-angiogenic agent(s); one or more agent(s) that promote the removal of abeta peptide from the brain; one or more agent(s) that inhibit amyloidogenesis; one or more agent(s) that restore tight junctions in cerebral vessels; or combinations thereof. Some embodiments provide for methods of promoting vascular reversion in the brain of a subject with Alzheimer's disease by administering an abeta peptide alone or in conjunction with one or more other therapeutic agent(s), for example, one or more anti-angiogenic agent(s).

In some embodiments, the invention provides for methods of identifying agents for the prevention and/or treatment of Alzheimer's disease that comprise testing the ability of a candidate agent to inhibit angiogenesis in the brain; maintain or restore BBB integrity and/or restore tight junctions in cerebral blood vessels.

Certain embodiments of the invention provide for diagnostic methods for identifying subjects at risk of developing Alzheimer's disease, or having early stage Alzheimer's disease, comprising detecting angiogenesis in the brain, tight junction (TJ) disruption and/or blood-brain barrier disruption in the brain of a subject.

Definitions

Unless defined otherwise, all technical and scientific terms used herein have the same meaning as commonly understood by one of ordinary skill in the art to which this invention belongs.

The terms "therapy" and "treatment," as used interchangeably herein, refer to an intervention performed with the intention of improving a subject's status. The improvement can be subjective or objective and is related to ameliorating the symptoms associated with, preventing the development of, or altering the pathology of a disease being treated. Thus, the terms therapy and treatment are used in the broadest sense, and include the prevention (prophylaxis), moderation, reduction, and curing of a disease at various stages. Preventing deterioration of a subject's status is also encompassed by the term. Subjects in need of therapy/treatment thus include those already having the disease as well as those prone to, or at risk of developing, the disease and those in whom the disease is to be prevented.

The terms "subject" and "patient" as used herein refer to an animal, such as a mammal or a human, in need of treatment.

As used herein, the term "about" refers to an approximately +/−10% variation from a given value. It is to be understood that such a variation is always included in any given value provided herein, whether or not it is specifically referred to.

Therapeutic Methods

One aspect of the invention provides for methods of treating or delaying onset of Alzheimer's disease through the use of anti-angiogenic agents and/or agents that prevent abeta amyloidogeneis and/or promote the removal of abeta peptide alone or in combination with additional therapeutic agents. In certain embodiments, there is provided methods of preventing and/or treating Alzheimer's disease by maintaining and/or restoring blood-brain barrier (BBB) integrity and/or restoring tight junction (TJ) integrity through the use of anti-angiogenic agents and/or agents capable of restoring TJ integrity and/or agents that prevent amyloidogenesis and/or promote removal of the abeta peptide. In accordance with the present invention, such agents include traditional small molecule drugs, as well as biologics, such as nucleic acid molecules, recombinant vectors, oligonucleotide inhibitors (aptamers, antisense and siRNA), peptides, proteins, antibodies and the like.

Examples of anti-angiogenic agents include, but are not limited to, HDAC inhibitors, valproic acid; anti-angiogenic chemokines (such as IP-10, PF-4 and MIP), cetuximab, panitumumab, PI3K/AKT/mTOR Pathway inhibitors, MAPK-Farnesyltransferase Rho and Ras Inhibitors, erlotinib, bexarotene, pazopanib (Votrient®); everolimus (Afinitor®); bevacizumab (Avastin®), imatinib, sorafenib, receptor tyrosine kinase inhibitors, 2 methoxyestradiol, sunitinib, leflunomide (SU101), midostaurin (PKC412), vatalinib (PTK787/ZK222584), AG013736, AZD2171, CP547,632, CP673,451, RPI.4610, VEGF Trap, ZD6474, YM359445, SU5416, temsirolimus (Torisel), batimastat, marimastat, neovastat, prinomastat, carboxyamidotriazole, fumagillin, TIMPs, TNP-470, CM101, IFN-α, IL-12, platelet factor-4, suramin, SU5416, thrombospondin, angiostatin, endostatin, thalidomide, tetrathiomolybdate, tecogalan, razoxane; isthmin; the dual Met/VEGF receptor 2 kinase inhibitor E7050; lycorine hydrochloride and reservatrol.

Examples of peptides that inhibit angiogenesis includes but are not limited to SPARC peptides; peptides derived from extracellular matrix proteins (such as Cilengitide (EMD 121974); Targeting RGD; ATN-161; Tumstatin Peptide; Tumstatin fragment; Pentastatin-1; Endostatin peptide; Endostatin fragment IV, IVox; Endostatin peptide fragment I (180-199); C16Y; C16S); peptides derived from Growth Factors or their receptors (such as VEGF derived peptide D(LPR) or KSVRGKGKGQKRKRKKSRYK; FGF-derived peptide Ac-ARPCA; P144 TSLDASIIWAMMQN); peptides derived from proteins involved in the coagulation cascade (such as B9870; HPRG derived ((HHPHG)$_4$); A-779; KV11; KPSSPPE; fibrinogen derived ARPAKAAATQK KVERKAPDA)); peptides derived from chemokines (such as PF4 derived (NGRKISLDLRAPLYKKIIKKLLES); Chemokinostatin-1; Anginex); Peptides derived from TSP1 domain containing proteins (such as DI-TSPa; ABT-510; ABT-526; Properdistatin); Peptides derived from serpin proteins (such as PEDF-TGA fragment; PEDF 34-mer fragment PEDF P18; SvOrth-2); pTnI; RC-3940-II; PAMP12-20; IM862; Aβ; Tetrastatin-1 (LPVFSTLPFAYCNI-HQVCHY); Tetrastatin-3 (AAPFLECQGRQGTCHFFAN); Pentastatin-3 (SAPFIECHGRGTCNYYANS); Thrombostatin con-3 (SPWSPCSGNCSTGKQQRTR); Chemokinostatin-7 (DGRKICLDPDAPRIKKIVQKKL); Chemokinostatin-8 (DGRELCLDPKENWVQRVVEKFLK); Semastatin-5 A.1 (GPWERCTAQCGGGIQARRR); Semastatin-5B (TSWSPCSASCGGGHYQRTR); Properdistatin (GPWEPCSVTCSKGTRTRRR); Scospondistatin (GP-WEDCSVSCGGGEQLRSR); Chemokinostatin-1 (NGRKACLNPASPIVKKIIEKMLNS); Chemokinostatin-3 (NGKKACLNPASPMVQKIIEKIL); Chemokinostatin-5 (NGKEICLDPEAPFLKKVIQKILD); Chemokinostatin-6 (NGKQVCLDPEAPFLKKVIQKILDS); Semastatin-5A.2 (SPWTKCSATCGGGHYMRTR); Nephroblastostatin (TEWTACSKSCGMGFSTRV); Wispostatin-1 (SP-WSPCSTSCGLGVSTRI); Thrombostatin con-1 (QP-WSQCSATCGDGVRERRR); Netrinstatin-5C (TEWS-VCNSRCGRGYQKRTR); Thrombostatin con-6, cyclic Cys4 and Cys8 (WTRCSSSCGRGVSVRSR); Wispostatin-2 (TAWGPCSTTCGLGMATRV); Wispostatin-3 (TK-WTPCSRTCGMGISNRV); Papilostatin-1(GPWAPC-SASCGGGSQSRS); Papilostatin-2 (SQWSPCSRTCGGGVSFRER); Hexastatin-2 (YCNI-NEVCHYARRNDKSYWL); Spondinstatin-1 (SEWSD-CSVTCGKGMRTRQR); Connectostain (TEWSACSK-TCGMGISTRV); Cyrostatin (TSWSQCSKTCGTGISTRV); Netrinstatin-5D (TEWS-ACNVRCGRGWQKRSR); Fibulostatin-6.1 (SAW-RACSVTCGKGIQKRSR); Fibulostatin-6.2 (AS-WSACSVSCGGGARQRTR); Fibulostatin-6.3 (QPWGTCSESCGKGTQTRAR); Cartilostatin-1 (SP-WSKCSAACGQTGVQTRTR); Cartilostatin-2 (GPWGPC-SGSCGPGRRLRRR); Adamtsostatin-4 (GPWGDC-SRTCGGGVQFSSR); Adamtsostatin-16

(SPWSQCTASCGGGVQTR); Adamtsostatin-18 (SK-WSECSRTCGGGVKFQER); Adamtsostatin-like 4 (SP-WSQCSVRCGRGQRSRQVR); Complestatin-C6 (TQWTSCSKTCNSGTQSRHR); Tetrastatin-2 (YCNI-HQVCHYAQRNDRSYWL); Hexastatin-3 (LPRFSTMPFI-YCNINEVCHY); (for review; see Rosca et al. Curr Pharm Biotechnol. 2011 Aug. 1; 12(8): 1101-1116).

Certain embodiments provide for methods of treating Alzheimer's disease through administration of an agent that inhibits VEGF, FGF, a FGF receptor, EGF, an EGF receptor, TGFβ (including but not limited to TGFβ1), a VEGF receptor, PDGF, a PDGF receptor, nitric oxide synthase, interleukin-6, interleukin-8, interleukin-1β, MMPs, TNFα or angiopoietin-2. Examples of such agents include, but are not limited to, bevacizumab (Avastin®), imatinib, sorafenib, sunitinib, leflunomide (SU101), midostaurin (PKC412), vatalinib (PTK787/ZK222584), AG013736, AZD2171, CP547,632, CP673,451, RPI.4610, VEGF Trap, ZD6474, YM359445, infliximab and reservatrol. Certain embodiments provide for methods of treating Alzheimer's disease through administration of an agent that stimulates γ-secretase activity and/or stimulates expression of Notch target genes.

Inhibition of the expression of angiogenic molecules through genetic methods, including the use of siRNA or antisense technologies is also contemplated. Inhibition of the activity of angiogenic molecules using peptides, antibodies, including single chain antibodies expressed by a vector, is also contemplated.

Some embodiments provide for methods of treating Alzheimer's disease through administration of an agent that inhibits neuropilin-1 or nestin, both of which have been shown to play a role in angiogenesis. Soluble neuropilin-1, for example, is known to decrease angiogenesis.

As demonstrated herein, removal of abeta peptide from the brain microvasculature results in vascular reversion and restoration of TJs. Accordingly, in one embodiment, the methods of promoting vascular reversion comprise administering an agent that removes abeta peptide, for example, an antibody or other compound that selectively binds abeta, or abeta itself. Some embodiments of the invention provide for methods of stimulating production of an endogenous antibody to the abeta peptide. Some embodiments provide for methods of promoting vascular reversion in the brain of a subject with Alzheimer's disease or at risk of developing Alzheimer's disease by administering an abeta peptide alone or in conjunction with another therapeutic agent, for example, an anti-angiogenic agent.

Disruption of the BBB is known to precede other pathologies in Alzheimer's disease. Accordingly, in certain embodiments, methods of delaying the onset of, or preventing, one or more disease pathologies associated with Alzheimer's disease by restoring blood-brain barrier integrity in a patient through administration of anti-angiogenic agents or agents that restore tight junctions in cerebral blood vessels. In some embodiments, methods of modifying disease outcome by the administration of such agents are provided.

Certain agents are known in the art to act on restoration of BBB and/or TJ integrity. Some embodiments of the invention provide for therapeutic methods that include the use of these agents. Examples of such agents include, but are not limited to, bryostatin-1, sodium butyrate, reservatrol, quercetin, decursin and clusterin. Glucocorticosteroids have also been demonstrated to restore BBB integrity (Marchi, et al., 2011, *Cardiovascular Psychiatry and Neurology, Vol. 201*, Article ID 482415) and are contemplated for use in the therapeutic methods of the invention.

Disruption of the BBB and TJs in Alzheimer's disease shows parallels to the disruption of the blood-retinal barrier (BRB) that occurs in wet macular degeneration. Accordingly, one embodiment of the invention provides for the use of agents used in, or in development for, the treatment of wet macular degeneration for treating Alzheimer's disease, including for example, VEGF inhibitors and anti-oxidants. Examples of such agents include, but are not limited to, Ranibizumab (Lucentis®), bevacizumab (Avastin®), Pegaptanib (Macugen®), VEGF Trap, Bevasiranib, Pazopanib (Votrient™), RTP801i-14//PF-655, AGN-745/SIRNA-027, Fenretinide, iSONEP™, and Evizon™.

Disruption of the blood-brain barrier and tight junctions is known to occur in multiple sclerosis (MS) and a number of agents have been developed for treatment of MS that improve the integrity of the BBB. Accordingly, one embodiment of the invention provides for the use of agents used in, or in development for, the treatment of MS for treating Alzheimer's disease. Examples include, but are not limited to, the interferon betas, such as interferon beta-1a (e.g. Avonex®, Rebif®, CinnoVex®) and interferon beta-1b (e.g. Betaferon®, Betaseron®, Extavia®, Ziferon®). In certain embodiments, the use of other MS treatments, such as, glatiramer acetate (Copaxone®), natalizumab (Tysabri®) and/or fingolimod (Gilenya®), is also contemplated in the therapeutic methods of the invention although the effects of these compounds on BBB integrity are less well documented.

The use of combinations of anti-angiogenic agents is also contemplated in certain embodiments of the invention, as are combinations of anti-angiogenic agents with other modalities of treatment, such as glucocorticosteroids, anti-oxidants, anti-inflammatories, immunotherapies and the like. Some embodiments of the invention provide for the use of a combination of anti-angiogenic agent(s) with abeta peptide immunization.

In certain embodiments, the patient or subject has no known risk factors associated with Alzheimer's disease or has not been identified as having a risk factor associated with Alzheimer's disease. In other embodiments, the patient or subject has been identified as having one or more risk factors associated with Alzheimer's disease. These risk factors include but are not limited to sedentary lifestyle, atherosclerosis, diabetes, wet form macular degeneration, stroke, hypercholesterolemia, cerebral amyloid angiopathy, cerebral vascular disease, hypertension, low blood pressure, concussions, surgery, chemotherapy, exposure to anesthetic, metabolic disorder or syndrome, Downs Syndrome, cataracs, loss of smell and taste, change in gate, change in cognition/memory performance and MRI determined brain volume (smaller size or change in size).

Diagnostic Methods

One aspect of the invention provides for diagnostic methods for identifying a subject at risk of developing Alzheimer's disease, or having early stage Alzheimer's disease, comprising detecting angiogenesis, TJ disruption and/or BBB disruption in the brain of a subject. Angiogenesis, TJ disruption and/or BBB disruption can be detected for example, by assaying a biological sample from a subject for a biomarker indicative of angiogenesis, TJ disruption and/or BBBB disruption, or by assaying neoangiogenesis, TJ disruption and/or BBB disruption using medical imaging techniques known in the art.

In the context of the present invention, a biological sample is a sample including a biological material. Specific non-limiting examples include blood, serum, plasma and cerebrospinal fluid. Biological samples also include biopsies, for example, brain tissue.

Examples of biomarkers that could be used to detect angiogenesis include, for example, circulating angiogenic factors, such as VEGF, FGF-2, MMP-9, IL-8, IL-6 and HGF; endothelial cell derived molecules, such as sVEGFR1, sVEGFR2, sVEGFR3, sTie-2 and VCAM-1; and other circulating proteins or peptides, such as endostatin and tumstatin.

Examples of biomarkers that could be used to detect TJ disruption include, for example, IL-8, cingulin, ZO-1, ZO-2, occludin, claudin-6, Lfc, and E-cadherins, including soluble forms or fragments of these proteins.

Biomarkers that can be detected in blood as an indicator of BBB disruption are usually proteins that are normally found in the cerebrospinal fluid (CSF). Examples of such biomarkers include, for example, transthyretin (see Marchi, et al., 2003, J. Neuroscience, 23(5): 1949-1955), S-100β and soluble junctional adhesion molecule-3 (sJAM-3) (see Zrabquer, et al., 2010, J. Immunol., 185(3):1777-1785).

Methods of detecting such biomarkers in a sample at the protein or DNA/RNA level are known in the art and include, for example, ELISA, Western blot, proteomics, various PCR-based techniques and various array technologies (see, for example, Ausubel et al. (1994 & updates) *Current Protocols in Molecular Biology*, Wiley & Sons, New York, N.Y., and *Current Protocols in Protein Science*, ed. Coligan, J. E., et al., Wiley & Sons, New York, N.Y.).

Suitable medical imaging techniques generally involve the administration (for example by intravenous or intrathecal injection) of a contrast agent or tracer that enhances vascular structures. Images are acquired prior to and at an appropriate time interval or intervals after administration of the contrast agent using the selected imaging method, for example, magnetic resonance imaging (MRI), positron emission tomography (PET), computed tomography (CT) or ultrasound. Examples of contrast agents and tracers include, but are not limited to, gadolinium chelate tracers, iodine-based tracers, $H_2^{15}O$ tracers and microbubbles, as well as tracers coupled to a monoclonal antibody or peptide against a vascular target.

Methods of monitoring the efficacy of a given treatment are also provided in one embodiment of the invention. Efficacy can be assessed for example by taking samples from a subject prior to treatment and at various time points after treatment and assaying the samples for a biomarker indicative of angiogenesis, TJ disruption and/or BBB disruption, as described above, in order to assess the effect of the treatment on angiogenesis, TJ disruption and/or BBB disruption. Alternatively, the subject can be submitted to medical imaging techniques to assay angiogenesis, TJ disruption and/or blood-brain barrier disruption, as described above, prior to treatment and at various time points after treatment in order to assess the effect of the treatment on angiogenesis, TJ disruption and/or blood-brain barrier disruption.

Screening Methods

One aspect of the invention provides for methods of identifying agents for the treatment of Alzheimer's disease by testing the ability of a candidate agent to restore tight junctions in cerebral blood vessels and/or promote vascular reversion. In some embodiments, the methods are employed to screen known anti-angiogenic agents for those capable of restoring tight junctions in cerebral blood vessels and/or promoting vascular reversion.

The screening methods can be carried out in vitro in an appropriate cell culture or in vivo in an appropriate animal model.

For in vitro testing, a culture of an appropriate cell line, such as, cerebral capillary endothelial cells, immortalized human brain endothelial cell line HCMEC/D3, human umbilical vein EC (HUVEC), Immortalized Human Microvascular Endothelial Cell Line HMEC-1, which can provide a functional in vitro model of the BBB, can be treated with an agent that disrupts TJs, for example serum or serum-derived factors (such as lysophosphatidic acid (LPA) and VEGF), IL-2, or interferon gamma. The culture is subsequently contacted with the candidate agent and the extent of TJ restoration measured after an appropriate time interval or intervals. TJ restoration can be assessed, for example, by immunohistochemical methods to determine the localization of TJ proteins such as ZO-1, occludin and claudins, by visual inspection under a microscope, or by transendothelial electrical resistance (TER).

For in vivo testing an appropriate animal model is used. Various animal models of Alzheimer's disease are known in the art (see, for example, *Handbook of Animal Models in Alzheimer's Disease*, Ed. G. Casadesus, 2011, IOS Press, Inc., Fairfax, Va.). Examples of suitable mouse models include the Tg2576 mouse model described in the Examples provided herein, as well as Bri-wt-Abeta1-42A, PDAPP, APP-London, $APP^{NLh/NLh}$, C3-3, R.1.40, APP23, Tg-CRDN8, APPDutch, Tg-SweD1, Tg-ArcSwe, APParc, PSAPP, 3×Tg-AD, 5×FAD, APP/PS1 K1 and TBA2.

In general, for in vivo testing, the test animals are divided into groups, including a test group and a control group, which does not receive the candidate agent. A positive control group which receives an agent known to restore TJ integrity can be included if desired. The candidate agent is administered to the test group and the animals are monitored regularly, for example to check for any outwardly manifested changes as a result of the treatment. After an appropriate period of time, the animals are sacrificed and the integrity of the TJs in the cerebral blood vessels assessed by standard techniques. For example, immunohistochemical methods can be used to determine the localization of TJ proteins such as ZO-1, occludin and claudins, or biopsied samples can be visually inspected under a microscope. Measurement of the permeability of the BBB to Evans blue dye can also be assessed, as can the effect of the candidate agents on biomarkers for BBB or TJ integrity, as described above.

In certain embodiments of the invention, there is provided methods of identifying agents which may be useful for the prevention and/or treatment of Alzheimer's disease by testing the ability of a candidate agent to inhibit angiogenesis. For example, the agents may be tested for their ability to inhibit endothelial cell proliferation or capillary tube formation. In certain embodiments there is provided methods of identifying agents which may be useful for the prevention and/or treatment of Alzheimer's disease by testing the ability of a candidate agent to inhibit expression of genes which encode angiogenic proteins or enhance expression of genes which encode inhibitors of angiogenesis. Reporter gene assays linking the promoters of genes of interest to report genes (such as fluorescent proteins) are known in the art. In certain embodiments, there is also provided methods of testing the ability of a candidate agent to inhibit angiogenesis. In specific embodiments the methods of testing, test the ability of a candidate agent to inhibit Abeta or amyloid induced angiogenesis. Methods of inhibiting angiogenesis are known in the art and include but are not limited to endothelial cell proliferation assays, capillary tube formation assays, CAM assays and corneal pocket assays.

To gain a better understanding of the invention described herein, the following examples are set forth. It will be understood that these examples are intended to describe illustrative embodiments of the invention and are not intended to limit the scope of the invention in any way.

EXAMPLES

Example 1: Concurrent Angiogenesis and Blood Brain Barrier Tight Junction Disruption in the Pathophysiology of Alzheimer's Disease Summary The study described in Example 1 was carried out to characterize cerebrovascular integrity in Tg2576 AD model mice that overexpress the human amyloid precursor protein (APP) containing the double missense mutations, found in a Swedish family, that causes early-onset AD, by examining the expression of tight junction (TJ) proteins, occludin and ZO-1, in conjunction with markers of apoptosis and angiogenesis. In aged AD mice, a significant increase in the incidence of disrupted TJs, compared to age matched wild-type littermates and young mice of both genotypes, was directly linked to an increased microvascular density but not apoptosis, which strongly supports abeta (amyloid-beta peptide)-triggered hypervascularity as the basis for BBB disruption. Hypervascularity in human patients was corroborated in a comparison of postmortem brain tissues from AD and controls. The results described here demonstrate that abeta mediates BBB disruption due to neoangiogenesis, resulting in the redistribution of TJs that maintain the barrier.

The objective of this study was to characterize the relationship between abeta and BBB integrity through TJ morphology in the Tg2576 AD mouse and find a mechanism that can explain BBB disruption in AD. The results of this study indicate that the Tg2576 mice have significant TJ disruption, which is directly related to an increased vascular density related to increased angiogenesis.

Materials and Methods:

Mice

Tg2576 transgenic (Tg/+) mice were used in this study. These mice express human APP695 containing the Swedish missense mutations (K670N/M671L) [Hsiao et al. (1996) Science 274: 99-102], under control of the hamster prion protein promoter (Taconic). Mice were maintained on mixed C57B16/SJL background by mating heterozygous Tg2576 males to C57B16/SJL F1 females. Wild-type (+/+) littermates were used as controls. Aged mice were 18 to 24 months of age while young mice were five months of age. Mice were fed standard lab chow and water ad libitum and kept under a 12 hour light/dark cycle.

Classification of Human Brain Tissues

Well-characterized tissue reference standards of postmortem medial cortical and hippocampal brain tissues were obtained from the Kinsmen Laboratory Brain Bank at the University of British Columbia (Vancouver, BC, Canada). Reference standards of brains from no disease (ND) and from AD patients were used. Classification of clinical and pathological histories of the respective patients were as described in [Jantaratnotai et al. (2010) Curr Alzheimer Res 7: 625-636].

Tissue Preparation

Mice were terminally anesthetized with Avertin (0.02 mL/1 g). Brains were rapidly excised, olfactory bulbs removed and post-fixed in 4% paraformaldehyde for four days at 4° C. The brains were then imbedded in paraffin and sectioned serially at 5 µm. Paraffin embedding, sectioning, and dewaxing were performed by Wax-it Histology Services Inc. (Vancouver, BC, Canada). For immunoblotting, brains were rapidly excised and the hippocampus and neocortex was isolated from both brain hemispheres using methods demonstrated by Hagihara et al. [Hagihara et al. (2009) J Vis Exp. 33: pii 1543].

Immunostaining

Dewaxed paraffin sections underwent antigen retrieval using a conventional stovetop pressure cooker using 20 mM Tris with 0.7 mM EDTA buffer (pH 9.0) at full steam for 2 minutes. Cooled slides were then incubated in blocking buffer (25% normal goat serum; 3% BSA; 0.3% Triton X-100, Sigma) for 1 hour at room temperature. Primary antibodies used included rabbit anti-ZO-1 (1:200, Invitrogen), mouse anti-ZO-1 (1:200, Invitrogen), rabbit anti-occludin (1:200, Invitrogen), rabbit anti-activated caspase-3 (1:1000, Imgenex), and mouse anti-human CD105 (1:20, DAKO). Primary antibody staining was performed overnight at 4° C. in staining buffer (10% normal goat serum; 3% BSA; 0.3% Triton X-100). Normal donkey serum was used when staining with goat primary antibodies. Secondary antibodies used were complimentary to the species of the primary conjugated with either Alexa Fluor dyes 488 or 568 (1:500, Invitrogen). Secondary antibody staining was performed at room temperature for 1 hour in staining buffer. TOTO-3 (1:10000, Invitrogen) was used for nuclear counterstaining. Sections were washed in PBS with 0.1% Tween-20 (Sigma) three times for 5 minutes each between staining steps. Stained sections were coverslipped using Fluoromount-G (Southern Biotech) and allowed to air dry in the dark overnight.

Human brain tissues were stained using methods described by [Ujiie (2003) et al. Microcirculation 10: 463-470]. Briefly, free-floating 30 µm thick sections were immunolabelled with an anti-laminin primary antibody (1:100, rabbit, Sigma). Sections were then treated with the appropriate biotinylated secondary antibodies (1:1000; DAKO) for 1 hour at room temperature, followed by incubation in avidin-biotinylated horseradish peroxidase complex (1:1000; ABC Elite, Vector Labs). Peroxidase labeling was visualized by incubation in 0.01% 3,3-diaminobenzidine (DAB; Sigma) solution. When a dark purple/black color developed, sections were washed, mounted on glass slides, air-dried and coverslipped with Entellan (EMD Biosciences).

Confocal and Quantitative Analysis of Tight Junction Morphology

Brain sections were analyzed from paraffin blocks from every fifth section. Images, taken on a Zeiss LSM510 Meta (Zeiss, Germany), were acquired with 16 slices, averaged four times, through the Z-plane using a 40×/1.3 oil-immersion Plan-Neoflaur objective. The composite projected image was imported into Adobe Photoshop at 600 dpi and optimized for contrast and brightness. Quantitative analysis of tight junction morphology was analyzed according to the methodology developed by Plumb et al. [Brain Pathol 12: 154-169]. Confocal data sets represented approximately 100 cerebral blood vessels from both young and aged Tg2576 and littermate controls in the frontal cortex and hippocampus. Individual vessels were scored as either normal (1) or abnormal (0) for ZO-1 expression. Normal ZO-1 expression was judged as strong, continuous, intense and linear staining. In contrast, abnormal ZO-1 expression was judged as weak, punctate and/or discontinuous staining. Abnormal ZO-1 blood vessel expression was compared to normal blood vessels found in normal control or in normal vessels in diseased brains. To minimize the recording of incomplete or undulating vessels as abnormal due to observed "gaps" in ZO-1 staining, evidence of vessel continuity was sought in the images. For example, the presence of stained nuclei (with TOTO-3) or punctate or diffuse ZO-1 remnants was used to localize the position of abnormal gaps along the vessel tract. The incidence of tight junction disruption was defined as the average percentage of blood vessels in a given region of brain that displayed abnormal tight junction morphology.

Microvessel Density Quantification in Mouse Tissues

Microvessel density (MVD) was quantified by confocal microscopy using the methods developed by Guo et al. [Angiogenesis 4: 187-191] with minor modifications. Using CD105 as a marker of angiogenic cerebrovasculature [Holley et al. (2010) Neurosci Lett 470: 65-70], images of optimal fluorescent intensity were acquired and analyzed using the Zeiss LSM510 Meta software. Areas within the brain section containing high density ("hotspots") [Weidner et al. (1991) N Engl J Med 324: 1-8] CD105 staining were imaged using the 20×/0.45 N-Achroplan objective using the confocal imaging parameters mentioned previously. The total fluorescence area (TFA) in $\mu m^2$ was integrated above background, by the software, for each hotspot. The average TFA from four different hotspots per mouse was quantified. The TFA was used as a numerical representation of the total microvessels stained by the CD105 antibody. The MVD of the imaged field was expressed as a ratio of the TFA to the total area of the image.

Microvessel Density Quantification in Human Tissues

MVD was quantified using the hotspot method, similar to how the MVD in the mice were quantified. Briefly, areas within a brain section containing high density ("hotspots") [Holley (2010) et al. Neurosci Lett 470: 65-70] laminin staining were imaged using a Olympus LCPlanFL 20×/0.40 Objective on a Zeiss Axioplan-2 light microscope equipped with a DVC camera (Diagnostic Instruments). MVD quantification was performed using ImageJ (Rasband, W. S., ImageJ v1.44p, U. S. National Institutes of Health, Bethesda, Md., USA, http://rsb.info.nih.gov/ij/, 1997-2011). A background threshold level was initially determined from an 8-bit grey scale, derived from an original black and white image, in control slides processed without primary antibody. The percentage of pixels having a staining intensity greater than the corresponding threshold was then used to integrate the percentage area occupied by laminin staining for each hotspot. The average percentage area occupied by laminin staining from four different hotspots per brain region per patient was quantified. The MVD of the imaged field was expressed as a percent area occupied by the laminin staining to the total area of the image.

Quantitative Western Blot Analysis

Isolated neocortex and hippocampal tissues were homogenized in 1% NP-40 lysis buffer (20 mM Tris-base (pH 8.8), 2 mM EDTA, 150 mM NaCl, 1% NP-40 with protease inhibitors (Roche)) using a QIAGEN TissueLyser II set at 19 Hz for 20 minutes. To shear genomic DNA, homogenized samples were passed ten times through a 21-gauge needle then incubated on ice for 30 minutes. The homogenate was centrifuged at 4° C. at 14000×g for 30 minutes. Protein concentrations from the supernatants were determined by BCA assay (Pierce) and samples were adjusted to final concentration of 30 μg per lane. Proteins were resolved in 10% SDS-PAGE gels according to standard practices Immunoblotting was performed on nitrocellulose membranes (Pall) using rabbit anti-occludin (1:1000, Invitrogen), mouse anti-human CD105 (1:1000, DAKO) and mouse anti-beta actin (1:1000, Santa Cruz). Alexa Fluor 680-conjugated anti-rabbit IgG (Invitrogen) and IRDye800 conjugated anti-mouse IgG (Rockland) were used as secondary antibodies. All antibody dilutions were made in milk protein solutions. Signal intensities were analyzed by using the Odyssey infrared image system (LICOR).

Statistical Analysis

All experiments were performed at least three times in triplicate. Statistical comparisons of data between aged and young Tg2576 AD mice and wild-type control littermates were performed with either Student's t-test or 2-way ANOVA for unmatched values with Bonferroni post-tests. All statistical analyses were performed using GraphPad Prism (v5.01 for Windows, GraphPad Software, San Diego Calif. USA, www.graphpad.com). p-values less than 0.05 were considered significant. Values are expressed as mean±SEM.

Results:

Tg2576 Mice have a Higher Incidence of Abnormal Cerebrovascular Tight Junction Morphology.

To assess changes in TJ morphology the staining patterns of occludin and ZO-1, both well-established TJ markers, were examined by confocal microscopy. TJ morphology was characterized in several brain regions including the neocortex, hippocampus and choroid plexus of wild-type and Tg2576 mice. Nearly all the observed blood vessels were sectioned longitudinally. Transverse blood vessels were rare. Strong, continuous and linear staining patterns of occludin and ZO-1 within the cerebrovasculature were considered normal, which was indistinguishable in both the cortex or hippocampus regardless of age or genotype [[FIG. 1: A, C, E and G]]. The faint outlining of the vessel track, enhanced by nuclear counterstaining, allowed junctional abnormalities to be easily spotted. Compared to controls, Tg2576 mice exhibited a higher incidence of punctate staining of occludin [[FIG. 1: B and F]] and ZO-1 [[FIG. 1: D and H]] in the neocortex and hippocampus, respectively. The choroid plexus, a region of the brain not affected in AD, exhibited normal TJ patterns for both occludin and ZO-1 in all mice (data not shown).

The TJ disruption was quantified by calculating the average percentage of blood vessels displaying abnormal morphology. The neocortex of aged Tg2576 mice showed a significant increase in TJ disruption (30.50±1.94%; ***p<0.001, 2-way ANOVA) compared to wild-type littermates (which averaged 10%) [[FIG. 2: A]]. There was also a significant difference in the incidence of TJ disruption between aged Tg2576 and young, Tg2576 mice (*p<0.05, 2-way ANOVA) [[FIG. 2: A]].

Similar results were seen in the hippocampus. Aged Tg2576 mice (24.75±2.32%; ***p<0.001, 2-way ANOVA) showed a significant increase in the incidence of TJ disruption compared to wild-type littermates (averaging 10%) [[FIG. 2: C]]. A significant increase in the incidence of TJ disruption was seen in aged Tg2576 mice compared to young Tg2576 mice (*p<0.05, 2-way ANOVA) [[FIG. 2: C]]. The amount of TJ disruption in young mice, in both the cortex and hippocampus, of both genotypes averaged approximately 10% and was not significant.

Occludin protein levels were examined by western blot in the neocortex and hippocampus of aged Tg2576 mice. In the cortex, the ratio of occludin to β-actin was reduced by nearly half [[FIG. 2: B]] in the transgenic mice (3.78±0.49) compared to the wild-type (6.81±0.80, p=0.0072, t-test). The hippocampus exhibited a similar reduction in the ratio of occludin to β-actin in the aged Tg2576 mice (5.89±0.76) compared to the wild-type (10.31±1.15, p=0.0076, t-test) [[FIG. 2: D]].

Aged Tg2576 Brains have Limited Apoptotic and Increased Angiogenic Cerebral Vascular Signals.

Figure 3:
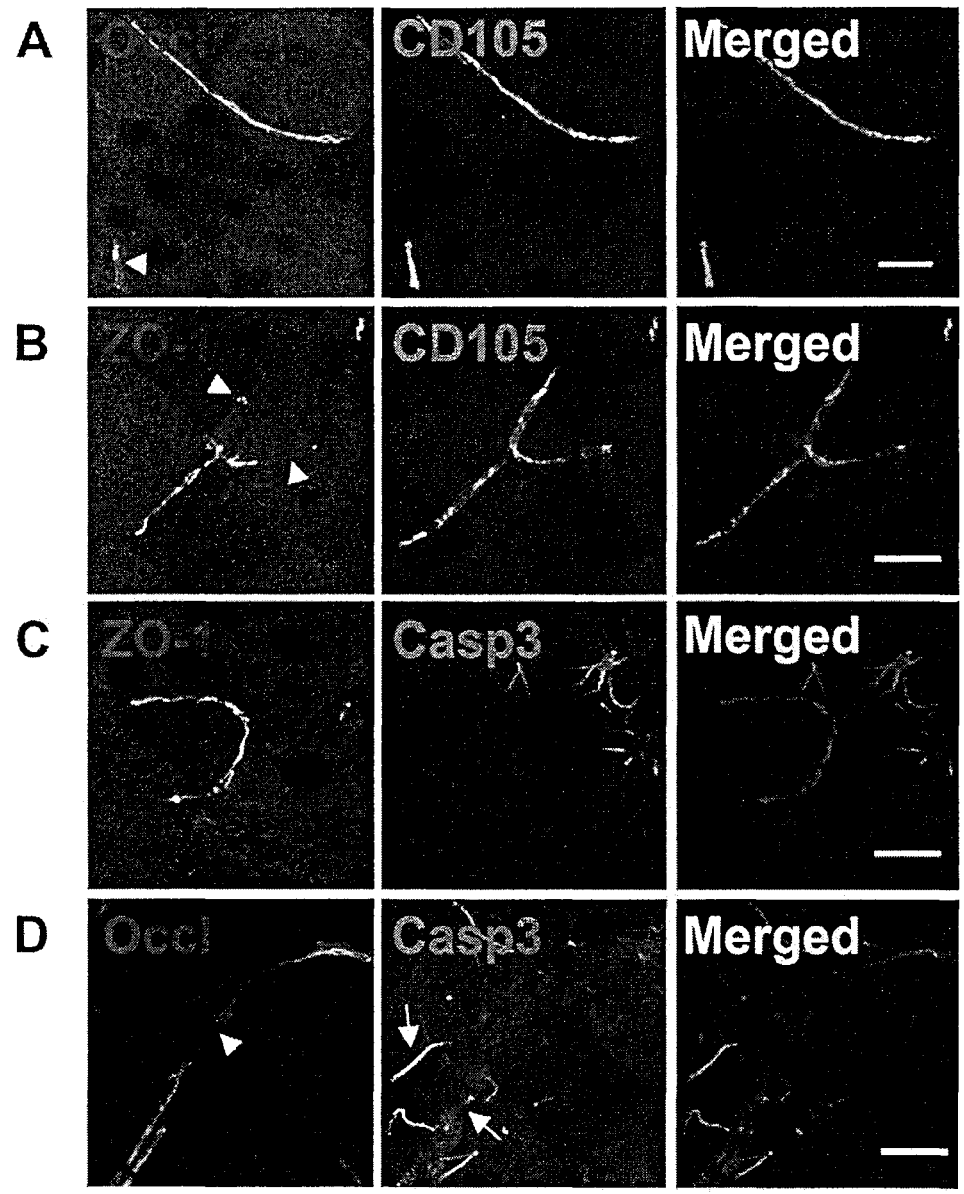
FIG. 3: Angiogenesis not apoptosis induces alterations in tight junction immunoreactivity in Tg2576 mice. This figure presents representative confocal micrographs of TJs (ZO-1), double stained for markers of angiogenesis or apoptosis in aged wild-type and Tg2576 mice. All vessels stained for CD105 regardless of the TJ expression pattern. White arrowheads point to regions of TJ abnormality in the vasculature. Double staining of blood vessels with ZO-1 (red) and CD105 (green) in wild-type (a) and Tg2576 (b) neocortex. Double staining of vessels with ZO-1 (red) and caspase 3 (green) in wild-type (c) and Tg2576 (d) neocortex. Caspase-3 staining did not colocalize with ZO-1 staining indicating an absence of apoptosis in the vasculature. E and F) Western blot analysis of CD105 and caspase 3. Results are representative of three separate experiments of three mice per group of brain tissues examined. Scale bar represents 20 μm.

Apoptosis and angiogenesis were explored as possible mechanisms to explain the observed brain vascular TJ abnormalities in the aged Tg2576 mice. Activated caspase-3 was used as a marker of apoptosis [[FIG. 3: C-E]]. In all examined sections, there was no activated caspase-3 immunoreactivity in endothelial cells. Activated caspase-3 staining was noted in other cell types and had a filamentous-like morphology. In young and aged wild-type mice, there was very limited activated caspase-3 staining within the neocortex [[FIG. 3: C]]. Blood vessels in the cortex and hippocampus that did exhibit TJ abnormalities, [[FIG. 3: D]], had neuronal-like staining that was directly adjacent to or overlapped with blood vessels [[FIG. 3: D (white arrows)]]. All mice had hippocampal staining of activated caspase-3 in the CA1, CA2, CA3 and DG regions to various degrees. Young Tg2576 and wild-type (both young and aged) had significantly higher activated caspase-3 staining densities within the hippocampus compared the cortex. The overall density of caspase-3 hippocampal staining in young Tg2576 and wild-type (all ages) mice was noted to be lower than aged Tg2576 mice. However, aged Tg2576 mice had significant activated caspase-3 staining within the both the neocortex and hippocampus that tended to center around probable plaque locations.

To assess for angiogenesis CD105, a well establish endothelial marker, was used [Duff et al. (2003) FASEB J 17: 984-992]. CD105 stained all vessels uniformly, regardless of age and genotype. However, a higher proportion of blood vessels were stained with CD105 in aged Tg2576 compared to age-matched wild-type littermates and young mice of both genotypes [[FIG. 3: B]].

Aged Tg2576 Mice have Increased Microvascular Density.

It was noted earlier that a higher proportion of blood vessels were stained with CD105 in aged Tg2576mice. The microvascular density (MVD) was quantified in the brains of young and aged Tg2576 mice and age-matched wild-type littermates by CD105 staining. The MVD was defined as a ratio of the TFA to the total area of an imaged field and was used as a surrogate measure of angiogenesis. Aged Tg2576 mice had a significantly higher MVD compared to wild-type. The average MVD in aged Tg2576 mice (0.4453±0.0146; ***p<0.001, 2-way ANOVA) was over double that of wild-type (0.1882±0.0010) [[FIG. 4: A]]. When compared to young Tg2576 mice, the MVD in aged Tg2576 was over 1.5 times (*p<0.05, 2-way ANOVA). Young Tg2576 mice had a trend towards a higher average MVD (0.2674±0.0161) but the differences were not significantly different compared to wild-type (0.2321±0.0110) [[FIG. 4: A]].

CD105 protein expression levels were quantified by western blot in both the neocortex and hippocampus of aged Tg2576 and wild-type mice. In the cortex, the ratio of CD105 to β-actin was nearly double [[FIG. 4: B]] in the Tg2576 mice (4.57±0.27) compared to that of the wild-type (2.52±0.27, ***p<0.001, t-test). The hippocampus exhibited a similar increase in the ratio of CD105 to β-actin in the aged Tg2576 mice (5.66±0.62) compared to the wild-type (3.53±0.46, *p<0.05, t-test) [[FIG. 4: C]].

In a preliminary examination of human tissues, quantifying the amount of laminin staining in the brains of no disease (ND) and AD patients was conducted in carefully validated cases from the Kinsmen Laboratory Brain Bank at University of British Columbia. These samples were used as reference standards of postmortem medial cortical and hippocampal brain tissues [Jantaratnotai et al. (2010) Curr Alzheimer Res 7: 625-636] to provide support that increased cerebral vascular density also extends from animal models of AD into clinical disease in humans In the cortex of the AD reference standard, the average MVD by percent area was nearly double (12.23±1.28%, *p<0.05, t-test) compared to the ND patient (7.25±1.25%) [[FIG. 4: D]]. Similarly, the hippocampus of the AD reference displayed a doubling in the average MVD (11.35±0.60%, ***p<0.001, t-test) compared to the ND reference (7.10±0.23%) [[FIG. 4: E]]. The extent of the increased cortical cerebral vascular density from laminin staining in the AD patient [[FIG. 4: G]] can be visually seen in the representative images compared to the ND patient control [[FIG. 4: F]. Hippocampal tissue displayed similar staining patterns in the AD and ND patients (data not shown).

Discussion

It has been previously established by quantification using the Evans Blue dye method that the BBB is compromised in the Tg2576 AD model mouse and that the breakdown can be rescued by immunization with abeta [Ujiie et al. (2003) Microcirculation 10: 463-470; Dickstein et al. (2006) FASEB J 20: 426-433]. The reduced BBB integrity preceding other AD neuropathology such as amyloid plaques, provided a strong link between brain vascularity and Alzheimer's disease (AD). However, the current dogma holds that BBB leakiness in AD is likely due to vascular deterioration and apoptosis. The goal of the study described in Example 1 was to test the hypothesis that angiogenesis and hypervascularization underlie increased vascular permeability in AD. The integrity of the BBB was assessed by examining TJ morphology in Tg2576 AD mice that express the human APP containing the double missense mutations, found in a Swedish family, that causes early-onset AD. Two separate age groups of mice were examined: five months old (prior to disease onset) and aged 18+ months old (well-after disease onset). Aged Tg2576 mice were found to have significantly abnormal TJ expression, compared to controls, which correlated with increased abhorrent angiogenesis. Taken together, abeta-influenced angiogenesis appears to cause BBB breakdown in Tg2576 mice at the level of TJs.

Recently it has come into question whether the large aggregated extracellular abeta plaques, a hallmark of AD pathology, directly cause the neurodegenerative effects in AD. It is now believed that the smaller, more toxic, soluble abeta oligomers directly initiate disease (reviewed in Sakono M, Zako T (2010) FEBS J 277: 1348-1358). The presence of these toxic oligomers could influence endothelial survival and TJ expression. Several lines of in vitro evidence have explored endothelial dysfunction by abeta. Marco et al. [Neurosci Lett 401: 219-224] demonstrated that abeta1-42 stimulated endothelial cultures induced aberrant expression of TJ proteins including claudins, occludins and ZO-1. Gonzalez et al. [Gonzalez-Velasquez et al. (2008) J Neurochem 107: 466-477] demonstrated that smaller abeta1-40 aggregates induced endothelial cell permeability and the relocalization of ZO-1 to the cytoplasm. Abeta induced reactive oxygen species (ROS) was ruled out as a potential cause of BBB leakiness because the presence of ROS detoxifying enzymes did not influence abeta induced damage [Nagababu et al. (2009) J Alzheimers Dis 17: 845-854]. However, the reorganization of cytoskeletal proteins was believed to directly influence BBB integrity [Nagababu et al. ibid.]. Although the involvement of abeta related production of ROS is currently under revision, ROS from other sources including microglial activation and inflammation and from serum leakage, could still have an effect on BBB integrity [Pun et al. (2009) *Free Radic Res* 43: 348-364].

A specific highly toxic dodecameric 56 kDa abeta oligomer has been directly implicated in memory loss in Tg2576 mice, referred to as "abeta*56" [Lesne et al. (2006) *Nature* 440: 352-357]. This oligomer emerges at about six months of age in the Tg2576 mice, when memory deficits first become apparent, but is absent in younger mice [Lesne et al. ibid.]. In the present study, five-month old mice had a trend towards increased abnormal vascular TJs. However, Tg2576 mice begin showing a loss of BBB integrity as early as four months of age [Ujiie et al. (2003) *Microcirculation* 10: 463-470]. During this time, a build-up of smaller less toxic oligomers could begin negatively influencing BBB integrity in this mouse. By six months of age, it is hypothesised that the toxic presence of abeta*56 initiates a cascade of the pathological events associated with the Tg2576 mouse. Although, between the ages of six to 13 months, the relative levels of abeta*56 remain constant in the Tg2576 mice [Lesne et al. ibid.]. During this time the eventual accumulation of plaques and dystrophic neurons is enough to cause further pathological loss in this mouse. This could explain the dramatic presence of abnormal cerebral vascular TJ expression in the aged Tg2576 mice.

In the study shown in Example 1, an antibody against activated caspase-3 failed to detect endothelial apoptotic events. However, young (5 months of age) and aged (18-24 months of age) Tg2576 and corresponding wild-type mice exhibited active caspase-3 expression with non-endothelial staining predominately within the hippocampus. These data are consistent with the absence of wide-spread endothelial cell death. Although, apoptotic endothelial cells were not observed in this study, in vitro evidence does suggest that abeta, especially mutations pertaining to the Dutch mutant, have been shown to induce apoptosis in cultured endothelial cells [ossati S, et al. (2010) FASEB J 24: 229-241; Miravalle et al. (2000) J Biol Chem 275: 27110-27116; Paris et al. (2005) Brain Res Mol Brain Res 136: 212-230].

Angiogenesis was also examined as another potential mechanism for TJ disruption in cerebrovascular endothelium. There are several lines of evidence that suggest angiogenesis occurs during AD. First, neuroinflammation is a pathological feature of AD [Streit W J, Mrak R E, Griffin W S (2004) *J Neuroinflammation* 1: 14] and is associated with the increase in cytokines, like IL-1β, that are capable of inducing angiogenesis [Pogue A I, Lukiw W J (2004) *Neuroreport* 15: 1507-1510]. The pro-angiogenic growth factor VEGF is also induced by these cytokines [Schultheiss et al. (2006) *Angiogenesis* 9: 59-65] and is elevated in AD patients [Tarkowski et al. (2002) Neurobiol Aging 23: 237-243]. VEGF directly stimulates endothelial proliferation [Shibuya M (2009) FEBS J 276: 4636-4643]. Abeta peptides themselves have also been shown to have angiogenic properties [Boscolo et al. (2007) Int J Mol Med 19: 581-587].

In the study described here, CD105 was used to examine angiogenesis in cerebral blood vessels labeled with the TJ markers. The antibody staining was not able to distinguish vessels with TJ abnormalities from those without [Duff et al. (2003) FASEB J 17: 984-992]. In this study, the apparent pan-endothelial staining of CD105 was extremely useful as it allowed the quantitation of the density of CD105 staining and thus the microvascular density (MVD), in the entire brain. The MVD was used as a surrogate marker for the amount of angiogenesis present within a given area of tissue section. The greater the vascular density, the more angiogenesis is believed to have occurred. Measuring the MVD is not without limitations which include a lack of standardization and reliance on the operator to minimize bias leading to the loss of objectiveness [Goddard et al. (2002) *Angiogenesis* 5: 15-20]. Nonetheless, aged Tg2576 mice had nearly double the MVD compared to age-matched wild-type mice. Young Tg2576 mice exhibited no significant differences in MVD but had a trend towards an increase in MVD compared to the controls.

Angiogenesis in the Tg2576 mouse is controversial. Paris et al [*Neurosci Lett* 366: 80-85] noted the Tg2576 mouse to have limited angiogenesis. The pan endothelial marker PECAM was used to quantify angiogenesis in mice up to 17 months of age. Although there is no consensus in the literature as to which is the "best" antibody, PECAM is not favoured as an angiogenic marker as compared to CD105 [El-Gohary et al. (2007) Am J Clin Pathol 127: 572-579] since PECAM is not limited to pan-endothelial expression as plasma and inflammatory cells are typically immunolabeled also [Giatromanolaki et al. (1999) Oncol Res 11: 205-212]. CD105 on the other hand has been shown to consistently react with endothelial cells [El-Gohary et al. ibid.], especially those undergoing angiogenesis, and does not react with stromal or inflammatory cells [Saad et al. (2003) J Gynecol Pathol 22: 248-253; Saad et al. (2004) Mod Pathol 17: 197-203]. The data presented herein, demonstrates that an increased CD105-related MVD does indirectly demonstrate that angiogenesis and TJ abnormalities are related in the Tg2576 mouse. Pro-angiogenic signals have been detected in the Tg2576 mouse. Elevated VEGF in the cortical tissue of 20 month old Tg2576 mice [Burger et al. (2009) Int J Dev Neurosci 27: 517-523] supports the hypothesis that angiogenesis occurs in this AD model. Finally, increased expression of markers associated with angiogenesis of cerebral vasculature has been observed in human AD brains: [Jantaratnotai (2010) Curr Alzheimer Res 7: 625-636] (laminin or von Willerbrand factor expression); [Desai et al. (2009) *J Neural Transm* 116: 587-597] (integrin αV-β3 expression); and in the APP23 AD mouse model (beta3-integrin subunit expression). The conclusions from these studies however, teach that angiogenesis is a result of vascular remodeling that takes place as a result of neuroinflammation leading to vascular damage and death.

In the study described here, evidence of cerebral vascular death in the Tg2576 mouse was not found, and in contrast, evidence of a massive increase in neovascularization in both the Tg2576 mouse was observed. Furthermore, a preliminary examination of well-characterized normal and AD reference standards of postmortem medial cortical and hippocampal brain tissues indicates that these tissues also exhibit significant hypervascularity in AD (FIG. 4F-G).

In summary, this study indicates that there is a significant increase in the disruption of TJ's in Tg2576 mice and that these disruptions manifest with age and with disease severity. These data support the model that TJ disruption results from increased vascular permeability that takes place during extreme neovascularization in AD, triggered by increased abeta production. These pathophysiological features are profound and severe, appear early in disease development, and rival tau and abeta as characteristic hallmarks of AD.

Example 2: Hypervascularity and Disrupted Tight Junctions are Resolved in Amyloid-Beta Immunized Alzheimer's Disease Mice Summary The study described in Example 2 characterizes cerebrovascular integrity in Tg2576 AD model mice by examining the expression of tight junction (TJ) proteins (occludin and ZO-1) in conjunction with markers of apoptosis and angiogenesis. In aged AD mice, a significant increase in the incidence of disrupted TJs was directly linked to an increased microvascular density but not apoptosis, which strongly supports hypervascularity as a basis for BBB dysfunction. Hypervascularity, TJs organization and BBB resealing are all resolved by vaccination with Abeta peptides.

This study demonstrated that in an active Abeta immunization AD mouse model BBB TJ integrity is related to the presence of abeta. Removing abeta from the brain parenchyma eliminates the microvascular related TJ pathology and resolves angiogenesis. Furthermore, the observed CAA related microhemorrhaging in the human immunization trials can be explained by the loss of the TJs in the affected blood vessels. This study connects vascular remodeling with AD and this redefinition may lead to improved therapeutic options for AD patients.

Materials and Methods

Mice

As described in Example 1.

Abeta Vaccination

Abeta vaccination was performed as described by (Dickstein et al. (2006) FASEB J 20, 426-433) using a protocol that was developed by Schenk et al. (*Nature* 400, 173-177). Briefly, two separate vaccination strategies were carried out, therapeutic and preventative. Prior to immunization, mice were bled from the saphenous vein and serum collected. In the preventative approach, mice were vaccinated beginning at 6 weeks of age and sacrificed at 12 months. Mice used in the therapeutic strategy were vaccinated beginning at 11 months of age and sacrificed at 15 months. Abeta peptide was freshly prepared from lyophilized powder for each set of injections. For immunizations, 2 mg of abeta (human abeta1-40, Bachem) was added to 0.9 mL of deionized water and thoroughly mixed. Then 100 μL of 10×PBS was added to obtain a final 1×PBS concentration. The solution was vortexed and placed at 37° C. overnight until use the next day. Abeta1-40 (100 μg antigen per injection) or PBS (control) was mixed 1:1 (v/v) with complete Freund's adjuvant (CFA) for the first immunization. This was followed by a boost with abeta1-40 (100 μg) or PBS mixed 1:1 (v/v) with incomplete Freund's adjuvant (ICFA) at two weeks and monthly thereafter. From the fifth immunization onward, straight PBS or abeta were injected. Injections were performed i.p.

Tissue Preparation

Mice were terminally anesthetized with ketamine/xylazine (100 mg/kg; 10 mg/kg). Brains were rapidly excised, olfactory bulbs removed and post-fixed in 4% paraformaldehyde for four days at 4° C. The brains were then imbedded in paraffin and sectioned serially at 5 μm. Paraffin embedding, sectioning, and dewaxing were performed by Wax-it Histology Services Inc. (Vancouver).

Immunostaining

Dewaxed paraffin sections underwent antigen retrieval using a conventional stovetop pressure cooker using 20 mM Tris with 0.7 mM EDTA buffer (pH 9.0) at full steam for 2 minutes. Cooled slides were then incubated in blocking buffer (25% normal goat serum; 3% BSA; 0.3% Triton X-100, Sigma) for 1 hour at room temperature. Primary antibodies used included rabbit anti-ZO-1 (1:200, Invitrogen), mouse anti-ZO-1 (1:200, Invitrogen), rabbit anti-occludin (1:200, Invitrogen), rabbit anti-activated caspase-3 (1:1000, Imgenex), and mouse anti-human CD105 (1:20, DAKO). Primary antibody staining was performed overnight at 4 C in staining buffer (10% normal goat serum; 3% BSA; 0.3% Triton X-100). Normal donkey serum was used when staining with goat primary antibodies. Secondary antibodies used were complimentary to the species of the primary conjugated with either Alexa Fluor dyes 488 or 568 (1:500, Invitrogen). Secondary antibody staining was performed at room temperature for 1 hour in staining buffer. TOTO-3 (1:10000, Invitrogen) was used for nuclear counterstaining. Sections were washed in PBS with 0.1% Tween-20 (Sigma) three times for 5 minutes each between staining steps. Stained sections were coverslipped using Fluoromount-G (Southern Biotech) and allowed to air dry in the dark overnight.

Confocal and Quantitative Analysis of Tight Junction Morphology

Brain sections were analyzed from paraffin blocks from every fifth section. Images taken on a Zeiss LSM510 Meta (Zeiss, Germany), were acquired with 16 slices, averaged four times, through the Z-plane using a 40×/1.3 oil-immersion Plan-Neofluor objective. The composite projected image was imported into Adobe Photoshop, at 600 dpi, and optimized for contrast and brightness. Quantitative analysis of tight junction morphology was analyzed according the methodology developed by Plumb et al. (*Brain Pathol* 12, 154-169). Confocal data sets represented approximately 100 cerebral blood vessels from both young and aged Tg2576 and littermate controls in the frontal cortex and hippocampus. Individual vessels were scored as either normal (1) or abnormal (0) for ZO-1 expression. Normal ZO-1 expression was judged as strong, continuous, intense and linear staining. In contrast, abnormal ZO-1 expression was judged as weak, punctate and/or discontinuous staining Abnormal ZO-1 blood vessel expression was compared to normal blood vessels found in normal control or in normal vessels in diseased brains. To minimize the recording of incomplete or undulating vessels as abnormal, due to observed "gaps" in ZO-1 staining, evidence of vessel continuity was sought in the images. For example, the presence of stained nuclei (with TOTO-3) or punctate or diffuse ZO-1 remnants was used to localize the position of abnormal gaps along the vessel tract. The incidence of tight junction disruption was defined as the average percentage of blood vessels in a given region of brain that displayed abnormal tight junction morphology.

Microvessel Density Quantification

Microvessel density (MVD) was quantified by confocal microscopy using the methods developed by Guo et al. (*Angiogenesis* 4, 187-191 with minor modifications). Using CD105 as a marker of angiogenic cerebrovasculature (Masliah et al. (2005) *Neurology* 64, 129-131), images of optimal fluorescent intensity were acquired and analyzed using the Zeiss LSM510 Meta software. Areas within the brain section containing high density ("hotspots") (Bombois et al. (2007) *Arch Neurol* 64, 583-587) CD105 staining were imaged using the 20×/0.45 N-Achroplan objective using the confocal imaging parameters mentioned previously. The total fluorescence area (TFA) in μm' was integrated above background, by the software, for each hotspot. The average TFA from four different hotspots per mouse was quantified. The TFA was used as a numerical representation of the total microvessels stained by the CD105 antibody. The MVD of the imaged field was expressed as a ratio of the TFA to the total area of the image.

Statistical Analysis

All experiments were performed at least three times in triplicate. Statistical comparisons of data between aged and young Tg2576 AD mice and wild-type control littermates were performed with either Student's t-test or 2-way ANOVA for unmatched values with Bonferroni post-tests. All statistical analyses were performed using GraphPad Prism (v5.01 for Windows, GraphPad Software, San Diego Calif. USA). p-values less than 0.05 were considered significant. Values are expressed as mean±SEM.

Results:

Immunized Tg2576 Mice Exhibit Reduced Cerebrovascular Tight Junction Pathology

Figure 5:
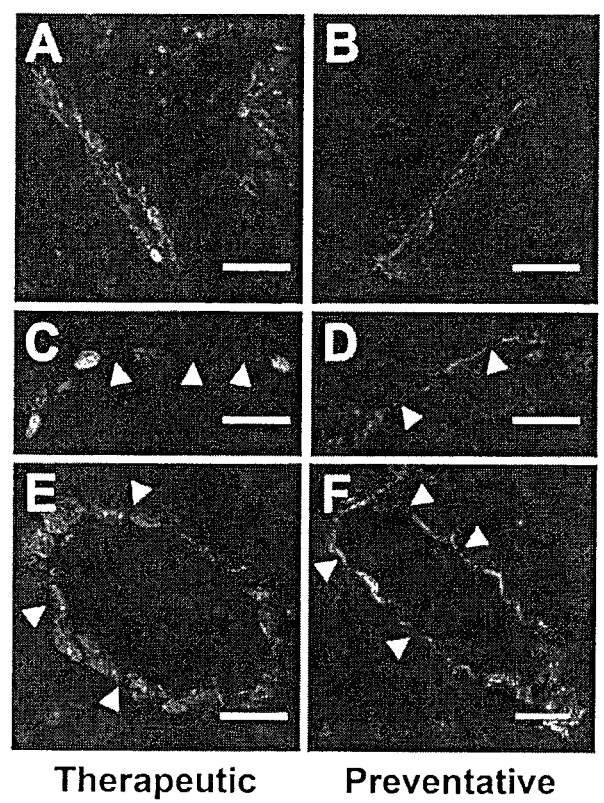
FIG. 5: Abeta and PBS immunized Tg2576 mice exhibit normal and abnormal TJ expression as assessed by confocal microscopy. Representative confocal micrographs of cerebral blood vessels from abeta immunized (preventatively or therapeutically) Tg2576 mice immunolabeled for either occludin or ZO-1 (red) and counterstained for DNA (blue) with TOTO-3. Normal tight junction expression had strong, continuous and linear occludin or ZO-1 expression in the blood vessels. (a) Normal occludin expression in the microvessels of the hippocampus of a Tg2576 mouse immunized with abeta therapeutically. (b) Normal ZO-1 expression in the microvessels of the cortex of a Tg2576 mouse immunized with abeta preventatively. Abnormal tight junction expression in blood vessels of the cortex and hippocampus displayed faint, punctate and discontinuous morphology (white arrowheads). (c) Abnormal ZO-1 expression in the cortex of a therapeutically immunized Tg2576 mouse. (d) Abnormal occludin expression in the hippocampus of a preventatively immunized Tg2576 mouse. (e) Large transversely sectioned vessels displaying abnormal occludin expression in a therapeutically immunized Tg2576 mouse. (f) Large transversely sectioned vessels displaying abnormal ZO-1 expression in a preventatively immunized Tg2576 mouse. Results are representative from three mice per group from three separate experiments. Scale bar depicts 20 μm.

Tight junction (TJ) morphology and pathology was characterized in the cortex and hippocampus of Tg2576 and wild-type mice immunized with either abeta or PBS. Strong, continuous and linear staining patterns of occludin and ZO-1 within the cerebrovasculature FIGS. 5a and b were considered normal, which was consistent and indistinguishable in either the cortex or hippocampus regardless of genotype, immunizing strategy or agent. Weak, punctate and or discontinuous staining patterns FIGS. 5c and d (white arrowheads) for both occludin and ZO-1 on the cerebrovasculature were considered abnormal. Expression of TJ abnormalities was consistent and indistinguishable in the cortex and hippocampus of all mice regardless of genotype, immunizing strategy or agent. Most of the observed microvessels in abeta immunized Tg2576 mice had normal TJs FIGS. 5a and b, while vessels displaying TJ abnormalities were rare. However, larger vessels in the Tg2576 mice immunized with abeta, either preventatively or therapeutically, appeared to have a larger proportion of abnormal TJ expression FIGS. 5e and f (white arrowheads) compared to the capillaries.

Figure 6:
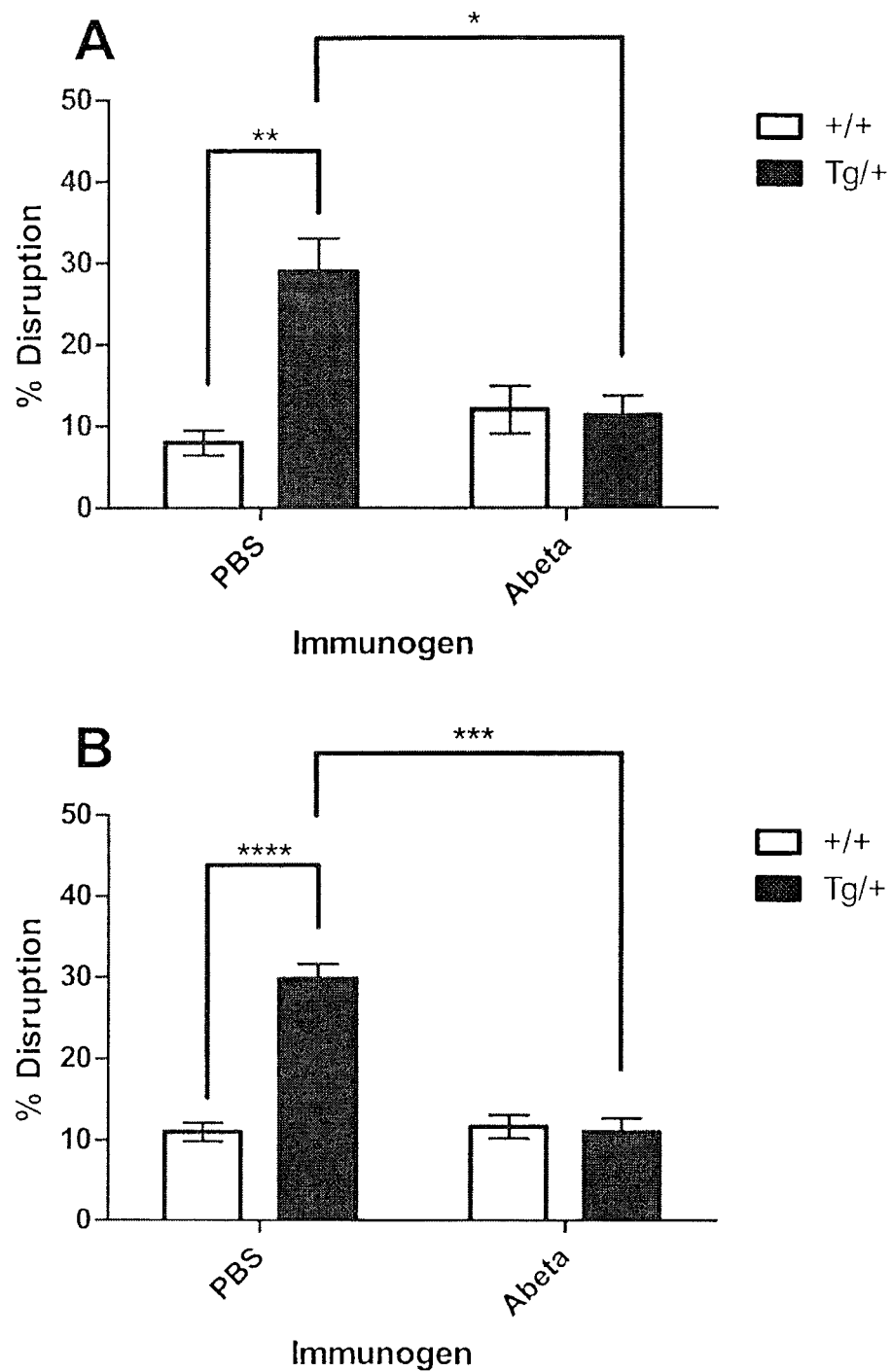
FIG. 6: Tg2576 mice immunized preventatively for one year with abeta had reduced tight junction abnormalities as compared to PBS immunized controls. The incidence of TJ abnormality in the (a) cortex and (b) hippocampus of Tg2576 (Tg/+) and wild-type (+/+) mice preventatively immunized with either PBS or abeta was compared quantitatively. Graphs depict the percentage of blood vessels expressing TJ abnormality, by ZO-1 expression patterns. In the (a) cortex, PBS immunized Tg/+ had significantly higher incidence of TJ disruption compared to PBS+/+ (** p=0.0080). The incidence of TJ disruption was also significantly higher in PBS Tg/+ compared to abeta immunized Tg/+ mice (* p=0.0188). In the (b) hippocampus PBS immunized Tg/+ had significantly higher incidence of TJ disruption compared to PBS+/+ (** p=0.0006). The incidence of TJ disruption was also significantly higher in PBS Tg/+ compared to abeta immunized Tg/+ mice (* p=0.0009). Values represent mean±SEM. PBS+/+, n=3; PBS Tg/+, n=4; abeta+/+, n=3; abeta Tg/+, n=3.

Quantitative Assessment of Cerebrovascular Tight Junction Pathology in Immunized Mice The incidence of TJ pathology was quantitatively assessed, by confocal microscopy, in Tg2576 mice immunized as part of a therapeutic or preventative strategy with either abeta or PBS. The incidence of TJ pathology was defined as the average percentage of blood vessels that displayed abnormal TJ morphology. The cortex of preventatively immunized PBS Tg2576 mice displayed a significantly higher percentage (29.00±4.02%; ** $p<0.05$, 2-way ANOVA) of disrupted TJ expression compared to PBS wild-type (about 10%) FIG. 6a. Abeta immunized Tg2576 mice displayed a significantly lower percentage of abnormal vascular TJ expression (11.33±2.40%; * $p<0.05$, 2-way ANOVA) compared to the PBS transgenic counterpart in the cortex FIG. 6a. The incidence of TJ disruption in the hippocampus mirrored the cortex for preventatively immunized mice. Tg2576 mice immunized with PBS displayed significantly higher disruption (29.75±1.89%; ** $p<0.05$, 2-way ANOVA) compared to PBS mice (about 10%) FIG. 6b. Hippocampal TJ disruption in abeta immunized Tg2576 mice were significantly lower (11.91±1.73%; * $p<0.05$, 2-way ANOVA) compared to PBS immunized Tg2576 mice FIG. 6b.

Figure 7:
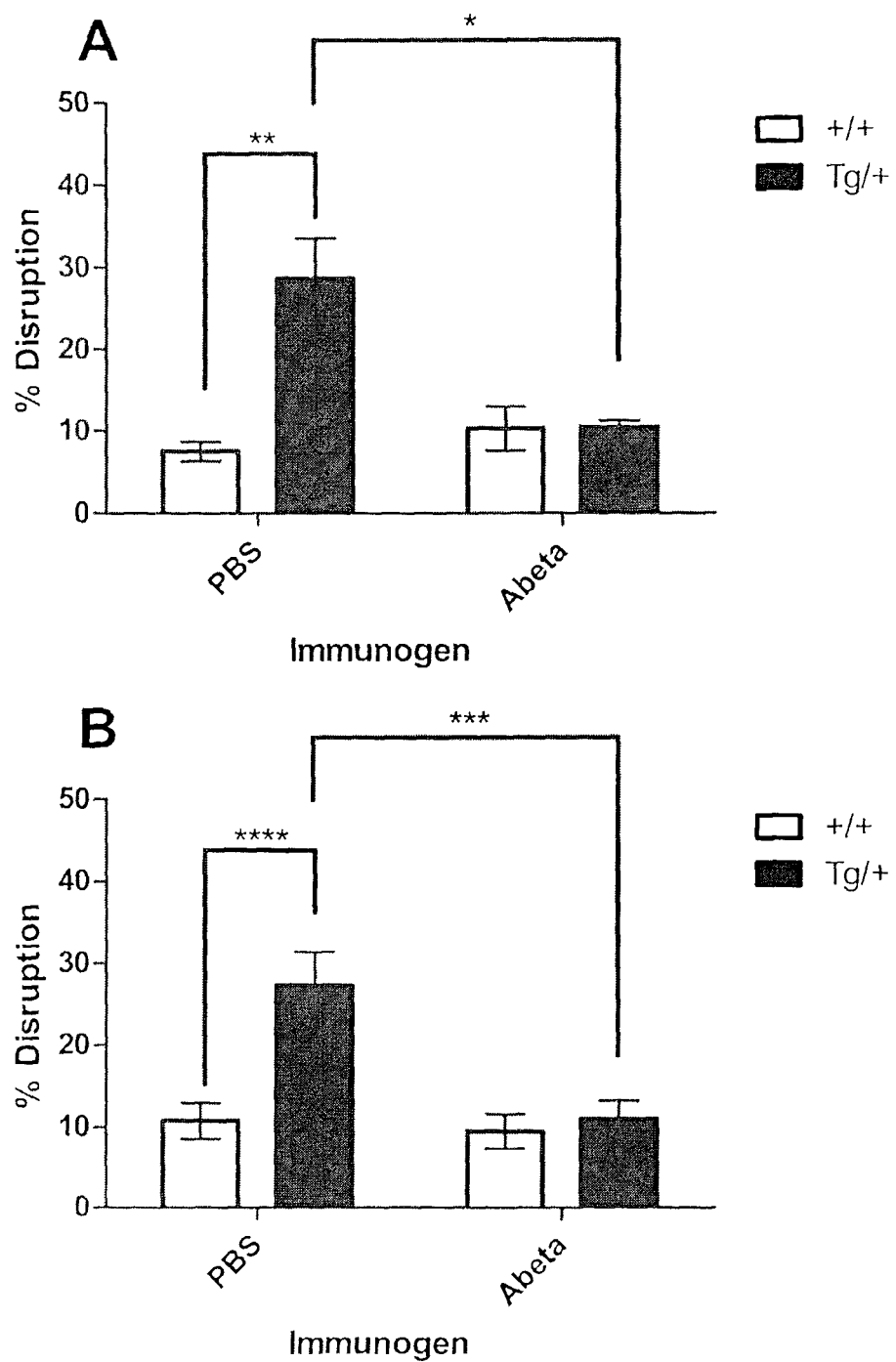
FIG. 7: Tg2576 mice immunized therapeutically for four months with abeta had reduced tight junction abnormalities as compared to PBS immunized controls. The incidence of TJ abnormality in the (a) cortex and (b) hippocampus of Tg2576 (Tg/+) and wild-type (+/+) mice therapeutically immunized with either PBS or abeta was compared quantitatively. Graphs depict the percentage of blood vessels expressing TJ abnormality, by ZO-1 expression patterns. In the (a) cortex, PBS immunized Tg/+ had significantly higher incidence of TJ disruption compared to PBS+/+ (** p=0.0046). The incidence of TJ disruption was also significantly higher in PBS Tg/+ compared to abeta immunized Tg/+ mice (* p=0.0028). In the (b) hippocampus PBS immunized Tg/+ had significantly higher incidence of TJ disruption compared to PBS+/+ (** p=0.0115). The incidence of TJ disruption was also significantly higher in PBS Tg/+ compared to abeta immunized Tg/+ mice (* p=0.0083). PBS+/+, n=4; PBS Tg/+, n=3; abeta+/+, n=4; abeta Tg/+, n=5. Values represent mean±SEM.

Therapeutically immunized mice displayed similar incidents of disrupted vascular TJs like that of the preventative mice. In the cortex of therapeutic immunized PBS Tg2576 mice displayed a significantly higher percentage of disrupted TJ expression (28.67±4.91%; ** $p<0.05$, 2-way ANOVA) compared to PBS wild-type (about 10%) FIG. 7a. Abeta immunized Tg2576 mice displayed a significantly lower percentage of abnormal vascular TJ expression (10.40±0.81%; * $p<0.05$, 2-way ANOVA) compared to the PBS transgenic counterpart in the cortex FIG. 7a. The incidence of TJ disruption in the hippocampus mirrored that of the cortex for therapeutic immunized mice. Tg2576 mice immunized with PBS displayed significantly higher disruption (27.33±4.06%; ** $p<0.05$, 2-way ANOVA) compared to PBS wild-type mice (about 10%) FIG. 7b. Hippocampal TJ disruption in abeta immunized Tg2576 mice were significantly lower (11.00±2.26%; * $p<0.05$, 2-way ANOVA) compared to PBS immunized Tg2576 mice FIG. 7b.

Abeta Immunized Tg2576 have Overall Reduced Cerebrovascular Leakage

Tg2576 and wild-type mice immunized, preventatively or therapeutically, with either abeta or PBS were assessed for cerebrovascular leakage and TJ abnormalities by confocal microscopy. Mouse albumin was used as a marker for vascular leakage and was visualized as diffuse gradient staining emanating away from vessels FIG. 8b (white arrowhead). Regardless of the immunizing strategy or agent, all wild-type mice examined had no vascular leakage and produced staining patterns similar to FIG. 8a. Tg2576 mice immunized with PBS, either preventatively or therapeutically, did not display any notable signs of vascular leakage in neither the cortex nor hippocampus. Vascular leakage in PBS immunized Tg2576 mice was associated with TJ abnormalities (not shown), as determined with staining with both occludin and ZO-1.

Figure 8:
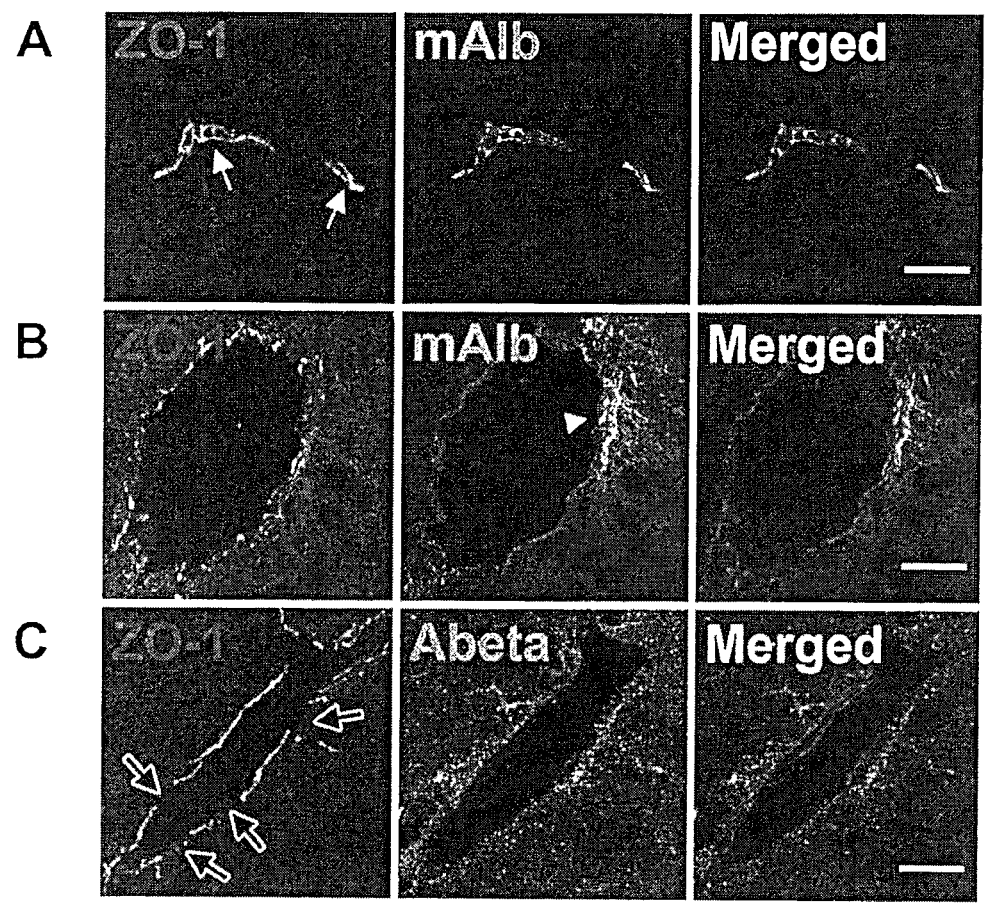
FIG. 8: Abeta immunized Tg2576 mice have overall reduced vascular leakage. Representative confocal micrographs of cerebral blood vessels from preventatively immunized Tg2576 mice with abeta immunolabeled for ZO-1 (red), mouse albumin (mAlb, green) or abeta (green). Microvessels (a) typically had normal ZO-1 expression and did not display albumin leakage. White arrows point to two normal and separate ZO-1 expressing microvessels. Albumin leakage was typically associated with larger vessels (b), which displayed TJ abnormalities. Leakage (white arrowhead) was represented as diffuse gradient like staining emanating away from vessels. (c) A large vessel with abnormal TJ expression (hollow white arrows) containing vascular deposition of abeta. Results are representative from three mice per group from three separate experiments. Scale bar represents 20 μm.

Tg2576 mice immunized with abeta had little to no vascular leakage within the microvessels FIG. 8a. However, the larger vessels of abeta immunized Tg2576 mice did have periodic vascular leakage FIG. 8b (white arrowhead). Abnormal TJ expression, both occludin (not shown) and ZO-1 FIG. 8b, was consistently seen in the larger vessels that had vascular leakage. To assess if the larger vessels from Tg2576 mice immunized with abeta had disrupted TJ pathology was associated with vascular abeta deposits, double staining for TJs and abeta was performed FIG. 8c. Mild vascular abeta deposition was seen in only the larger vessels in both the preventative and therapeutic abeta immunized Tg2576 mice. Large vessels that had vascular deposition of abeta also had TJ, both occludin (not shown) and ZO-1 FIG. 8c (hollow white arrows), pathology. No abeta deposition was seen in the cerebral capillaries in the abeta immunized Tg2576 mice. Treated wild-type had no vascular abeta. PBS treated Tg2576 for either one year or four months had very limited vascular abeta.

Angiogenesis and Apoptosis in Immunized Tg2576 Brains

Figure 9:
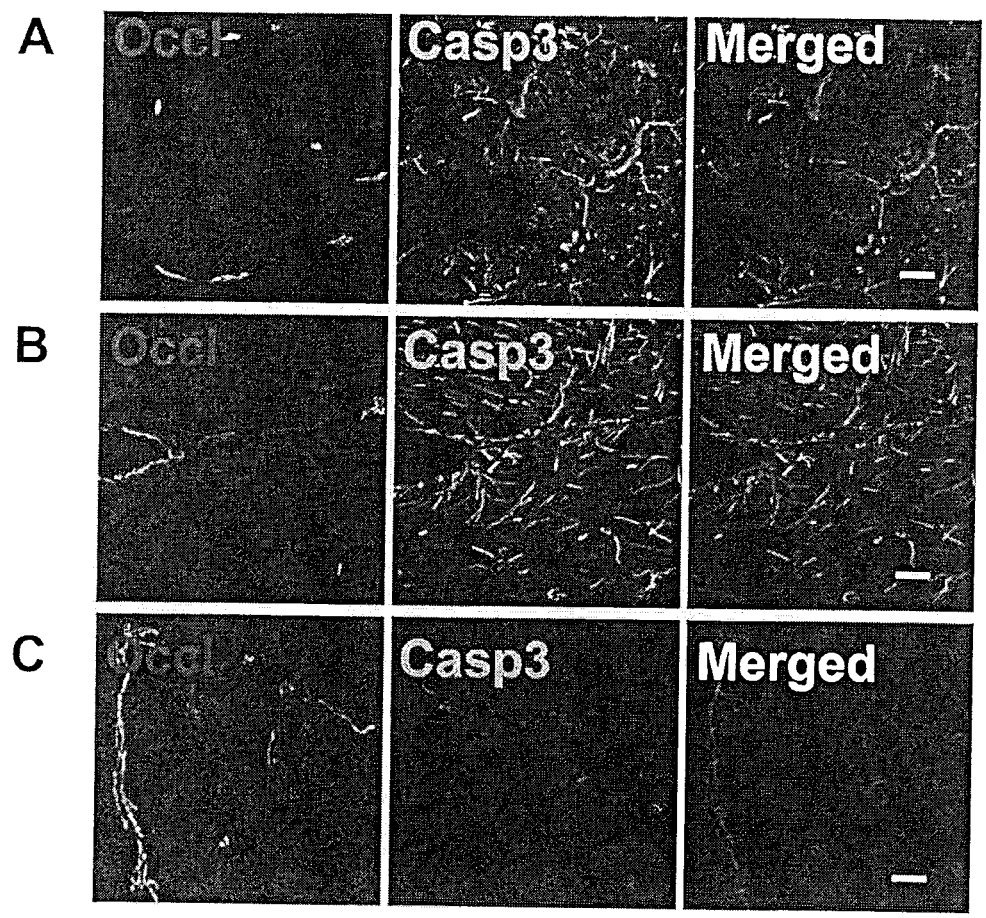
FIG. 9: Abeta immunized Tg2576 mice have reduced activated caspase-3 staining. Representative confocal micrographs (taken at 20×) depict activated caspase-3 staining (casp3, green) with occludin (occlu, red) TJs. (a) Activated caspase-3 staining in the cortex of PBS therapeutically immunized Tg2576 mice surround TJ halos. (b) Activated caspase-3 staining within the hippocampus of a wild-type mouse immunized preventatively with abeta. Filamentous-like structures probably corresponding to neurons can be seen in green. No overlap or containing was seen with either occludin or ZO-1 labeled blood vessels. (c) Activated caspase-3 staining in the cortex of an abeta therapeutically immunized Tg2576 mouse. Limited caspase-3 staining can be seen in this region of the brain. Results are representative from three mice per group from three separate experiments. Scale bar represents 20 μm.

Incidents of apoptosis and angiogenesis were examined, by confocal microscopy, in Tg2576 mice immunized preventatively or therapeutically with either abeta or PBS. An anti-activated caspase-3 antibody was used as a marker of apoptosis FIG. 9. In all examined sections, activated caspase-3 did not directly stain the endothelia. Similar to the staining patterns noted in aged and young Tg2576 mice, activated caspase-3 was seen in filamentous-like cell bodies that were presumed to be neurons. All immunized mice exhibited activated caspase-3 staining in the hippocampus, albeit in various amounts, in the CA1, CA2, CA3 and DG regions. PBS immunized Tg2576 mice, both preventative and therapeutic, had significant activated caspase-3 staining within the FIG. 9a cortex and hippocampus (not shown) that tended to surround probable abeta plaques. Wild-type (abeta and PBS) and abeta immunized Tg2576 mice exhibited hippocampal restricted caspase-3 staining FIG. 9b. The overall density of activated caspase-3 staining in these mice was noted to be lower than the Tg2576 treated with abeta. The cortex of abeta immunized, both preventative and therapeutic, Tg2576 had limited caspase-3 staining FIG. 9c. Cortex activated caspase-3 staining appear similar in the abeta immunized Tg2576 to the wild-type variants. These results were consistent across all mice examined.

Figure 10:
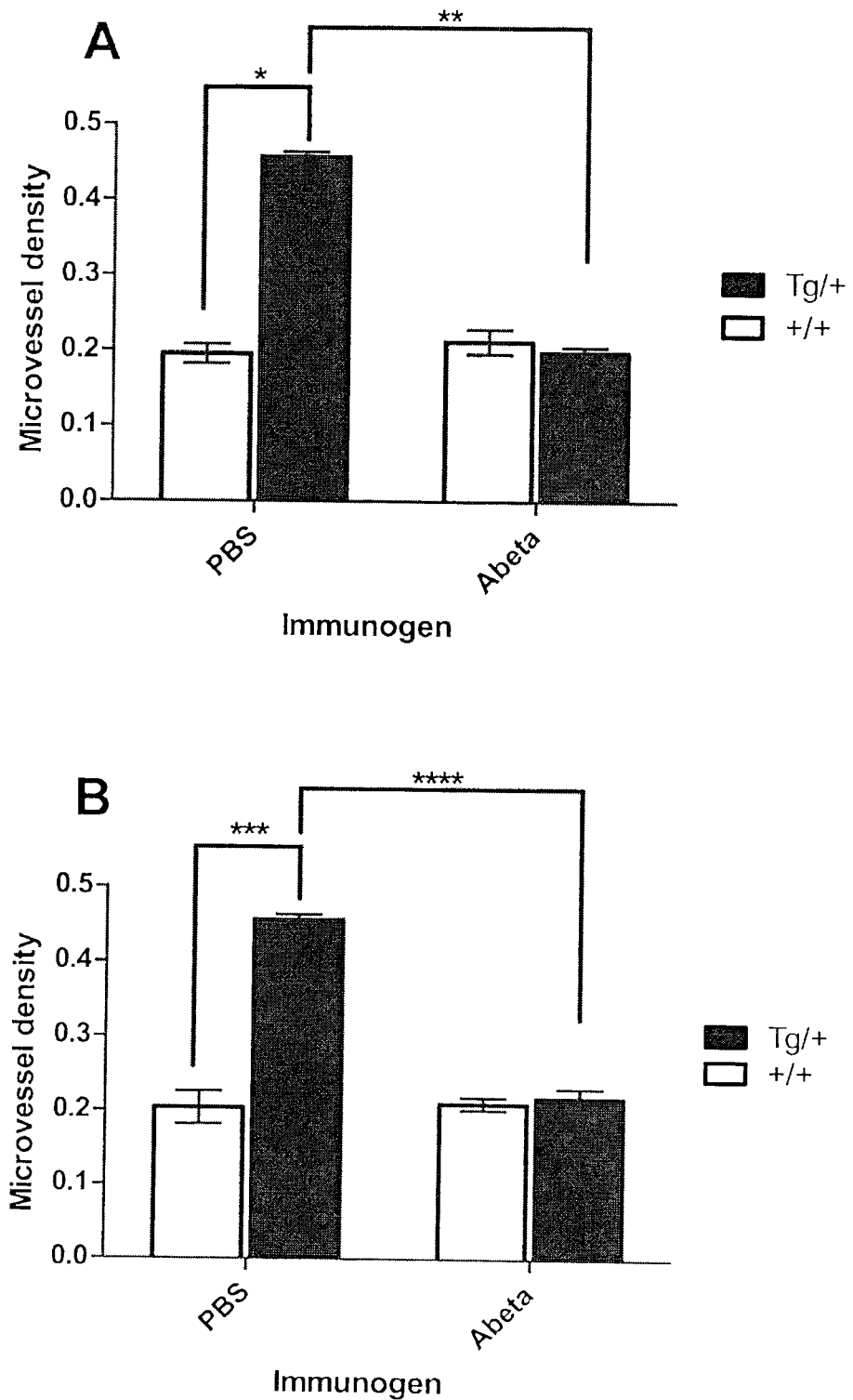
FIG. 10: Abeta immunized Tg2576 mice have reduced microvascular density compared controls. The MVD in the cerebrovasculature of abeta and PBS immunized, preventatively and therapeutically, Tg2576 (Tg/+) and wild-type (+/+) mice was quantified by CD105 staining (a) Preventatively immunized Tg/+ mice with PBS had significantly increased MVD compared to the PBS immunized+/+ (* p<0.0001, t-test). Abeta immunized Tg/+ had a significantly reduced MVD compared to the Tg/+ immunized with PBS ( p<0.0001, t-test). PBS+/+, n=4; PBS Tg/+, n=4; abeta+/+, n=4; abeta Tg/+, n=4. (b) Therapeutically, immunized Tg/+ with PBS had significantly increased MVD compared to the PBS immunized+/+ (* p=0.0001, t-test).). Abeta immunized Tg/+ had a significantly reduced MVD compared to the Tg/+ immunized with PBS (**** p<0.0001, t-test). PBS+/+, n=5; PBS Tg/+, n=4; abeta+/+, n=4; abeta Tg/+, n=3. Values represent mean±SEM.

CD105 staining was used as an angiogenic endothelial marker; however, CD105 staining was seen on all the brain vasculature regardless of the absence or presence of TJ abnormalities. The microvessel density (MVD), by CD105 staining, was quantified by confocal microscopy in the mice immunized as part of the therapeutic or preventative strategy with either abeta or PBS. The MVD was defined as a ratio of the TFA to the total area of an imaged field and was used as a surrogate measure of angiogenesis. The average MVD in Tg2576 mice immunized with PBS for either preventatively for one year (0.4560±0.0072; * p<0.0001, t-test) was significantly higher compared to the wild-type immunized with PBS (0.1951±0.0123) FIG. 10a. Tg2576 mice immunized preventatively with abeta had a significantly reduced MVD (0.1972±0.0075;  p<0.0001, t-test) compared to transgenic immunized with PBS FIG. 10a. The MVD in the therapeutically immunized mice was similar to the preventative group. The average MVD in Tg2576 mice immunized with PBS for either therapeutically for four months (0.4939±0.0077; * p=0.0001, t-test) was significantly higher compared to the wild-type immunized with PBS (0.2044±0.0222) FIG. 10b. Tg2576 mice immunized therapeutically with abeta had a significantly reduced MVD (0.2180±0.0130; **** p<0.0001, t-test) compared to transgenic immunized with PBS FIG. 10b.

Discussion

It has been previously shown that mice immunized with abeta, either preventatively or therapeutically, elicited an immune response to the peptide as measured through an increase in anti-abeta antibody titres (Dickstein et al. (2006) FASEB J 20, 426-433). Pathologically, these abeta immunized Tg2576 mice had significantly reduced plaque burdens and microgliosis. These findings were consistent with previously published results using similar AD mice models and immunotherapy methods and show that the global integrity of the BBB improves significantly in post-abeta immunized Tg2576 mice.

The question addressed in this study was whether the improved BBB extends down to the level of the TJs. Abeta immunized Tg2576 mice were shown to have a markedly reduced TJ pathology in the microvasculature. The reduction in TJ pathology was seen in both the neocortex and hippocampus, which are normally heavily affected during AD (Hsiao et al. (1996) Science 274, 99-102; Braak & Braak, E. (1991) Acta Neuropathol 82, 239-259). Serum mouse albumin leakage from the microvessels of abeta immunized Tg2576 mice was minimal. However, increased mouse albumin leakage was noted in the larger vessels, which displayed TJ abnormalities and mild vascular deposition of abeta. Although mild vascular abeta deposition and serum leakage was qualitatively noted in this study, Wilcock et al. (J Neuroinflammation 1, 24) described significant increases in CAA and CAA-related microhemorrhaging in the passive immunization of the same AD mouse strain. This difference is most likely attributed to the age of the mice used in the respective vaccination studies. In the current study, mice immunized preventatively were sacrificed at one year. Mice immunized therapeutically were sacrificed at 15 months. Vascular deposition in the Tg2576 mouse is known to be fairly "intermediate" at 15 months (Domnitz et al. (2005) J Neuropathol Exp Neurol 64, 588-594). The Tg2576 immunized mice in the Wilcock et al. study noted above were vaccinated beginning at 23 months of age, when CAA is known to be "widespread" (Domnitz et al. (2005) J Neuropathol Exp Neurol 64, 588-594). Taken together, cerebrovasculature TJ disruption is directly related to the presence of abeta, whereby preventing the accumulation of abeta allows the microvasculature to repair any damage.

Several hypotheses have been proposed to explain the mechanism(s) of abeta immunotherapy. Briefly, the most popular mechanisms are microglial removal of abeta plaques, catalytic dissolution and the peripheral sink hypothesis. The mechanism of microglial removal of abeta has been summarized (Morgan, D. (2009) CNS Neurol Disord Drug Targets 8, 7-15). Briefly, peripheral circulating anti-abeta antibodies enter the brain and opsonize plaques. Microglia, the resident brain macrophages, removes plaques via Fc-receptor mediated phagocytosis. Catalytic dissolution involves peripheral circulating anti-abeta antibodies binding to and disrupting abeta aggregation by disrupting tertiary structure of the plaque (Solomon et al. (1997) Proc Natl Acad Sci USA 94, 4109-4112). The final mechanism is the peripheral sink hypothesis (DeMattos et al. (2001) Proc Natl Acad Sci USA 98, 8850-8855). In this mechanism, circulating anti-abeta antibodies bind and sequester plasma abeta, which disrupts the equilibrium of abeta efflux-influx through the BBB. The net result is the removal of abeta from the brain. This mechanism has gained favour recently due to increased incidence of CAA and related microhemorrhages in human trials of abeta immunotherapy (Masliah et al. (2005) Neurology 64, 129-131; Nicoll et al. (2006) J Neuropathol Exp Neurol 65, 1040-1048; Nicoll et al. (2003) Nat Med 9, 448-452; Ferrer et al. (2004) Brain Pathol 14, 11-20). CAA is an independent disease where abeta is deposited on vasculature resulting in the thickening of cerebral arteries and is described as a protein-elimination-failure arteriopathy (Weller et al. (2009) Alzheimers Res Ther 1, 6). Abeta that is removed from the brain as a result of immunotherapy is deposited in the arteries and thus exacerbates the observed immunotherapy related CAA (Weller et al., ibid). It is debatable as to which if any of these mechanisms plays a prominent role in abeta reduction or clearance. However, a combination of all three of the mechanisms is likely.

A side effect observed in the failed clinical abeta immunization trial was CAA-associated cerebral microhemorrhaging (Boche, D., Zotova, E., Weller, R. O., Love, S., Neal, J. W., Pickering, R. M., Wilkinson, D., Holmes, C., and Nicoll, J. A. (2008) Brain 131, 3299-3310). Several studies have noted microhemorrhaging in a variety of AD mouse models on the brain vasculature after active (Wilcock et al. (2007) Neuroscience 144, 950-960; Petrushina et al. (2008) J Neuroinflammation 5, 42; Wilcock et al. (2009) J Neurosci 29, 7957-7965) and passive immunization (Pfeifer et al. (2002) Science 298, 1379; Racke et al. (2005) J Neurosci 25, 629-636; Wilcock et al. (2004) J Neuroinflammation 1, 24). Disruption of the cerebrovasculture TJs does explain this side effect in relation to the peripheral sink hypothesis. The following abeta removal model is proposed. Pre-immunization, the abundance of abeta influences the integrity of the BBB endothelia resulting in the disruption of the TJs. Microvascular leakage ensues. During immunization, various abeta clearance mechanisms are activated including microglia removal and antibody dissaggregation. As the abeta plaques are dissolved, solubilized abeta is removed from the brain parenchyma along perivascular drainage routes (Weller et al. (2009) Alzheimers Res Ther 1, 6). For unknown reasons, the perivascular drainage of abeta is halted and becomes deposited in the cerebral arteries, resulting in CAA. The primary abeta species found deposited in the CAA-affected vasculature is more soluble abeta1-40, believed to be of neuronal origin (Herzig et al. (2006) Brain Pathol 16, 40-54). The deposition of abeta damages the surrounding endothelial TJs creating the observed microhemorrhages that could be mediated abeta induced ROS derived from NADPH-oxidase (Park et al. (2005) J Neurosci 25, 1769-1777). This model appears to be echoed in the failed human AD abeta immunization trial (Boche et al. (2008) Brain 131, 3299-3310).

Endothelial apoptosis, as measured by activated caspase-3 staining, was not seen in any of the mice via activated caspase-3 staining. All immunized mice, wild-type and Tg2576, had extensive activated caspse-3 staining in the hippocampus, which appeared to be neuronal-like. The presence of hippocampal activated caspase-3 in both wild-type and Tg2576 mice is consistent with a previous study (Niu et al. (2010) Neurosci Bull 26, 37-46). However, PBS immunized Tg2576 had extensive neuronal-like activated caspase-3 throughout the cortex and hippocampus. Much of the caspase staining was centered on plaque associated TJ (specifically ZO-1) halos. Abeta immunized Tg2576, lacking plaque pathology, had caspase-3 staining within the hippocampus only. Although the exact nature of cell death that occurs during AD is still controversial, apoptosis is believed to play a significant role (Rohn, T. T., and Head, E. (2008) Caspase activation in Alzheimer's disease: early to rise and late to bed. Rev Neurosci 19, 383-393). Furthermore, the Tg2576 mouse is not known to exhibit neuronal loss (Irizarry et al. (1997) J Neuropathol Exp Neurol 56, 965-973). The presence of cortex activated caspse-3 in control treated Tg2576 mice suggests that increased signals for apoptosis are present, likely due to abeta. Once abeta is removed, it is presumed the apoptotic signals are reduced.

Abeta immunization also appeared to modulate angiogenic signals in treated mice. Angiogenesis can be quantified through the average microvesicular staining densities of CD105 in the brain (Holley et al. (2010) Neurosci Lett 470, 65-70; Barresi et al. (2007) Acta Neuropathol 114, 147-156). The relative amount of angiogenesis was quantified by the MVD of CD105 staining. PBS treated Tg2576 mice, both preventatively and therapeutically, had significantly higher vascular densities compared to wild-type mice and abeta treated Tg2576 mice. This implies that angiogenic signals are reduced when abeta is removed. It is presumed that neuroinflammation is reduced as a result of amyloid immunotherapy. Microglia are believed to a significant source of neuroinflammation in neurodegenerative disease (Perry et al. (2010) Nat Rev Neurol 6, 193-201). A reduction in both neuroinflammation and abeta may directly or indirectly reduce angiogenic signals associated with both (Pogue, A. I., and Lukiw, W. J. (2004) Neuroreport 15, 1507-1510; Naldini, A., and Carraro, F. (2005) Curr Drug Targets Inflamm Allergy 4, 3-8; Boscolo et. al. (2007) Int J Mol Med 19, 581-587). Contrary to the current study, a passive immunization study using APP+PS1 mice examined neurogenesis related angiogenesis (Biscaro et al. (2009) J Neurosci 29, 14108-14119). After passive immunization in the transgenic AD mice, angiogenesis was found to be increased in the hippocampus, by BrdU staining, which can label cells undergoing DNA repair (Schmitz et al. (1999) Acta Neuropathol 97, 71-81) as opposed to angiogenic (replicating) vessels.

Example 3: Vascular Reversion in Alzheimer's Disease Follows Amyloid-beta Immunization Alzheimer's disease (AD) is an incurable neurodegenerative disorder and is the leading cause of dementia in the elderly (Castellani et al., Dis Mon 56, 484-546 (2010)). A key neuropathological hallmark of AD is the presence of extracellular neuritic plaques comprised of the amyloid beta peptide (Aβ) (Castellani et al., Dis Mon 56, 484-546 (2010)). Recent studies link neurovascular dysfunction (Zlokovic, Nat Rev Neurosci 12, 723-738 (2011)) with vascular risk factors (Dickstein et al., Mt Sinai J Med 77, 82-102 (2010)) in playing integral roles in the pathogenesis of AD. Vaccinations with Aβ, can dramatically reduce amyloid deposition, and prevent memory loss in transgenic mouse models of Alzheimer's disease. Recently, we proposed that amyloidogenesis promotes extensive neoangiogenesis leading to increased vascular permeability and subsequent hypervascularization in AD (Biron et al., PLoS ONE 6, e23789 (2011)). Here we test the hypothesis that immunization can resolve this pathophysiological feature of AD. We demonstrate that active AP immunization resolves plaque burden and neutralizes the amyloid trigger that leads to angiogenesis and reverses hypervascularity in an AD mouse model. These data support the conclusion that neoangiogenesis is a key process underlying plaque formation in AD. This appears to be the first example of vascular reversion following any therapeutic intervention and supports the conclusion that neoangiogenesis modulation may repair damage in the AD brain.

Aβ immunotherapy has received considerable attention as an AD modifying treatment strategy (Morgan, J Intern Med 269, 54-63 (2011)) due to various AD mouse models being successfully treated (Golde et al., CNS Neurol Disord Drug Targets 8, 31-49 (2009)). Supplementing these finds, we have previously demonstrated that active Aβ immunization restores blood-brain barrier (BBB) integrity in an AD mouse model (Dickstein et al., FASEB J 20, 426-433 (2006)). The overall positive effects of the preclinical animal studies of Aβ immunization encouraged a clinical human trial by Elan/Wyeth in late 1999 (Wilcock & Colton, J Alzheimer's Dis 15, 555-569 (2008)). The incomplete clinical trial had mixed results including reduced plaque pathology but persistent taupathies and neuroinflammation (Masliah et al., Neurology 64, 129-131 (2005)). The unexpected side effects seen in early human clinical trials demonstrate that our knowledge of Aβ and AD pathogenesis is incomplete.

Methods:

Mice:

As described in Example 1.

Abeta Vaccination:

As described in Example 2.

Tissue Preparation:

Tissues were prepared as previously described by Dickstein et al. (FASEB J 20, 426-433 (2006)). Mice were terminally anesthetized with ketamine/xylazine (100 mg/kg; 10 mg/kg) and perfused with PBS for 5 minutes. Brains were then rapidly excised, olfactory bulbs and cerebellum removed, weighed and post-fixed in 4% paraformaldehyde for four days at 4° C. The brains were then imbedded in paraffin and sectioned serially at 5 µm. Paraffin embedding, sectioning, and dewaxing were performed by Wax-it Histology Services Inc. (Vancouver). Average brain weights were compared amongst the immunized mice by comparing brain to body mass ratios.

Immunostaining:

Dewaxed paraffin sections underwent antigen retrieval using a conventional stovetop pressure cooker using 20 mM Tris with 0.7 mM EDTA buffer (pH 9.0) at full steam for 5 minutes. Cooled slides were then incubated in blocking buffer (25% normal goat serum; 3% BSA; 0.3% Triton X-100, Sigma) for 1 hour at room temperature. Primary antibodies used included rabbit anti-ZO-1 (1:200, Invitrogen), mouse anti-human CD105 (1:20, DAKO), and mouse anti-Aβ$_{1-16}$ (6E10) (1:2000, Covance). Primary antibody staining was performed overnight at 4 C in staining buffer (10% normal goat serum; 3% BSA; 0.3% Triton X-100). Secondary antibodies used were complimentary to the species of the primary conjugated with either Alexa Fluor dyes 488 or 568 (1:500, Invitrogen). Secondary antibody staining was performed at room temperature for 1 hour in staining buffer. TOTO-3 (1:10000, Invitrogen) was used for nuclear counterstaining. Sections were washed in PBS with 0.1% Tween-20 (Sigma) three times for 5 minutes each between staining steps. Stained sections were coverslipped using Fluoromount-G (Southern Biotech) and allowed to air dry in the dark overnight.

Confocal and Quantitative Analysis of Tight Junction Morphology:

Brain sections were analyzed from paraffin blocks from every fifth section. Images were taken on a Zeiss LSM510 Meta (Zeiss, Germany) using a 40×/1.3 oil-immersion Plan-Neoflaur objective. The composite projected image was imported into Adobe Photoshop, at 600 dpi, and optimized for contrast and brightness. Quantitative analysis of tight junction morphology was analyzed according the methodology described previously. Confocal data sets represented approximately 100 cerebral blood vessels from both young and aged Tg2576 and littermate controls in the frontal cortex and hippocampus. Individual vessels were scored as either normal (1) or abnormal (0) for ZO-1 expression. Normal ZO-1 expression was judged as strong, continuous, intense and linear staining. In contrast, abnormal ZO-1 expression was judged as weak, punctate and/or discontinuous staining. Abnormal ZO-1 blood vessel expression was compared to normal blood vessels found in normal control or in normal vessels in diseased brains. To minimize the recording of incomplete or undulating vessels as abnormal, due to observed "gaps" in ZO-1 staining, evidence of vessel continuity was sought in the images. For example, the presence of stained nuclei (with TOTO-3) or punctate or diffuse ZO-1 remnants was used to localize the position of abnormal gaps along the vessel tract. The incidence of tight junction disruption was defined as the average percentage of blood vessels in a given region of brain that displayed abnormal tight junction morphology. Aβ was imaged with a Zeiss LSM 710 Laser Scanning Microvessel Density Quantification:

Microvessel density was quantified by confocal microscopy using the methods described previously Biron et al., PLoS ONE 6, e23789 (2011)). Using CD105 as a marker of angiogenic cerebrovasculature (Holley et al. Neurosci Lett 470, 65-70 (2010)), images of optimal fluorescent intensity were acquired and analyzed using the Zeiss LSM510 Meta software. Areas within the brain section containing high density ("hotspots") CD105 staining were imaged using the 20×/0.45 N-Achroplan objective using the confocal imaging parameters mentioned previously. The total fluorescence area (TFA) in $\mu m^2$ was integrated above background, by the software, for each hotspot. The average TFA from four different hotspots per mouse was quantified. The TFA was used as a numerical representation of the total microvessels stained by the CD105 antibody. The microvascular density of the imaged field was expressed as a ratio of the TFA to the total area of the image.

Statistical Analysis:

Statistical comparisons of data between Tg2576 (Tg/+) AD mice and wild-type (+/+) control littermates in the different immunization strategies using PBS and Aβ were performed with 2-way ANOVA for unmatched values with Bonferroni post-tests.

All experiments were performed at least three times in triplicate. Statistical comparisons between Tg2576 (Tg/+) AD mice and wild-type (+/+) control littermates immunized with PBS or Aβ in the different immunization strategies were performed with 2-way ANOVA for unmatched values with Bonferroni post-tests. All statistical analyses were performed using GraphPad Prism (v5.01 for Windows, GraphPad Software, San Diego Calif. USA, www.graphpad.com). p-values less than 0.05 were considered significant. Values are expressed as mean±SEM.

Figure 11:
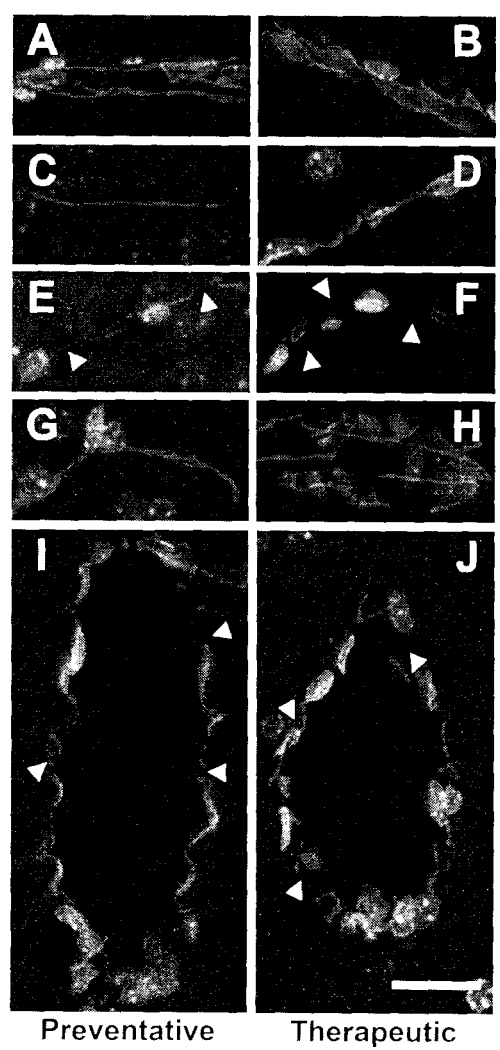
FIG. 11: Abeta immunized Tg2576 mice have normal TJ morphology. Representative images of cerebravasculature from abeta or PBS immunized (preventatively and therapeutically)+/+ and Tg/+ mice immunolabeled for ZO-1 (red) and counterstained for DNA (blue). Normal ZO-1 expression had strong, continuous and linear staining patterns as seen in +/+, PBS (A and B), +/+, (C and D) and Tg/+, (G and H). Normal ZO-1 in transversely (H) sectioned vessels produced near-parallel lines. Abnormal ZO-1 staining patterns appeared punctate, interrupted or discontinuous (white arrowheads) as seen in the small vessels of Tg/+, PBS (E and F) and larger vessels of Tg/+, (I and J). Scale bar represents 20 μm.

Immunized Tg2576 Mice Exhibit Reduced Cerebrovascular Tight Junction Pathology:

Does Aβ immunization restore TJ integrity? ZO-1 expression patterns were assessed in cerebrovasculature of the neocortex and hippocampus of Tg2576 (Tg/+) mice and wild-type (+/+) littermates immunized with Aβ and PBS both preventatively and therapeutically. Normal TJ expression was visualized as strong, continuous and uninterrupted staining patterns. Abnormal expression was ascertained as weak, punctuate and/or discontinuous staining. Indistinguishable regardless of brain region, +/+ mice immunized with either Aβ or PBS had normal ZO-1 staining patterns (FIG. 11a-d). Tg/+ mice immunized, preventatively and therapeutically, with Aβ exhibited normal ZO-1 expression in the capillaries (FIGS. 11g and h) similar to +/+ mice. Rare but normal transversely sectioned blood vessels had short generally parallel (FIG. 11h) or radial (not shown) arms of ZO-1 expression. Tg/+ mice receiving PBS had marked TJ pathology (FIGS. 11e and f). Interestingly, Tg/+ mice immunized with Aβ displayed some abnormal TJ pathology mainly in larger vessels (FIGS. 11i and j). The shift in ZO-1 pathology from the capillaries to the larger vessels in the AP immunized Tg/+ mice seems to mimic the increased CAA pathology observed in other AD immunotherapy models and clinical observations (reviewed by Vasilevko et al., Annals of the New York Academy of Sciences 1207, 58-70 (2010)).

Figure 12:
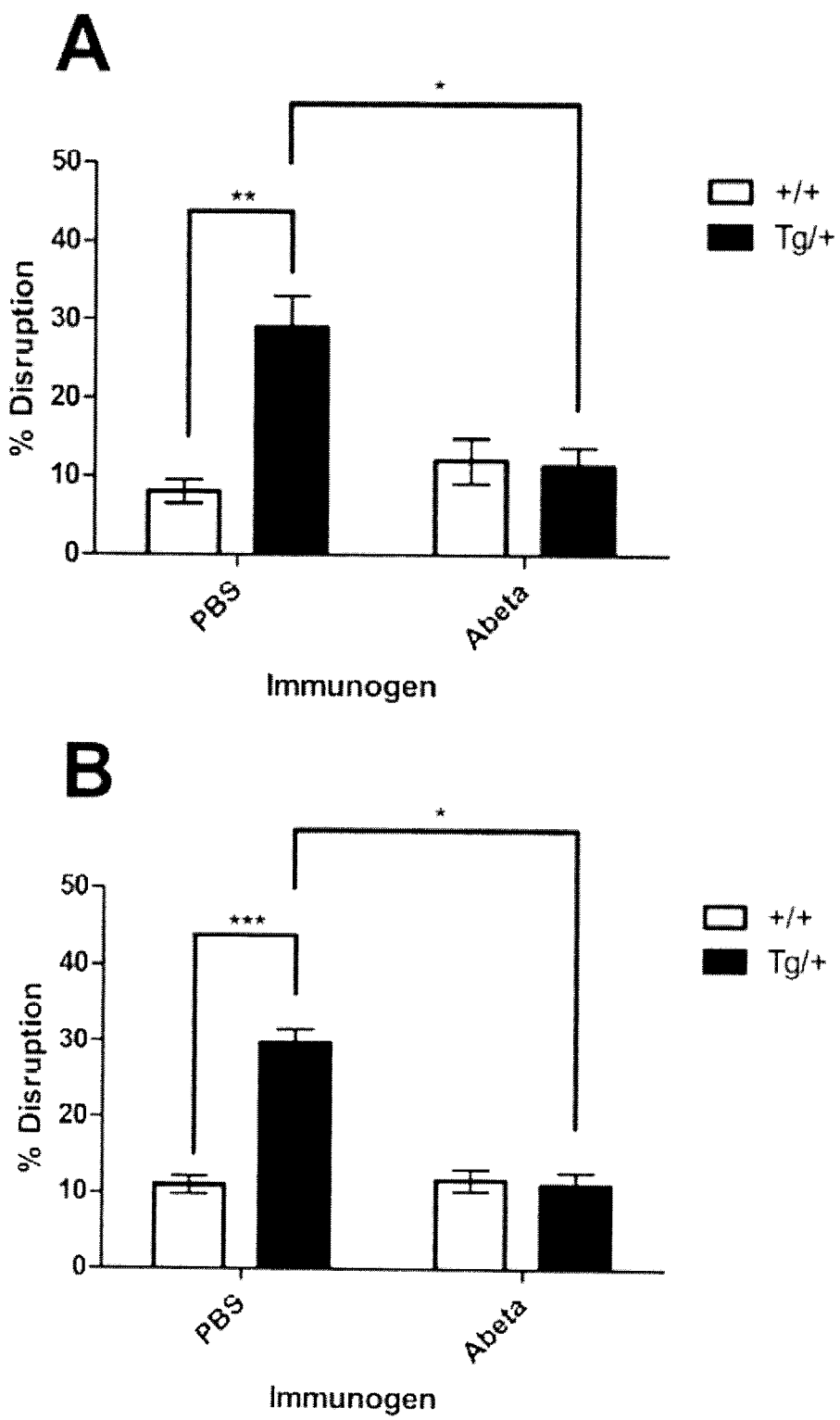
FIG. 12: Aβ immunized Tg2576 mice had reduced tight junction abnormalities. The percentage of blood vessels with abnormal ZO-1 expression patterns was significantly increased in Tg/+, PBS compared to Tg/+, Aβ and +/+, PBS immunized mice. These findings were consistent between immunization strategies, (a and b) preventative and (c and d) therapeutic, and brain regions, (a and c) cortex or (b and d) hippocampus. In the preventative strategy: +/+, PBS, n=3; Tg/+, PBS, n=4; Aβ, +/+, n=3; Tg/+, Aβ, n=3. In the therapeutic strategy: +/+, PBS, n=4; Tg/+, PBS n=3; +/+, Aβ, n=4; Tg/+, Aβ, n=5. * p<0.05,  p<0.01, * p<0.001.
Figure 12:
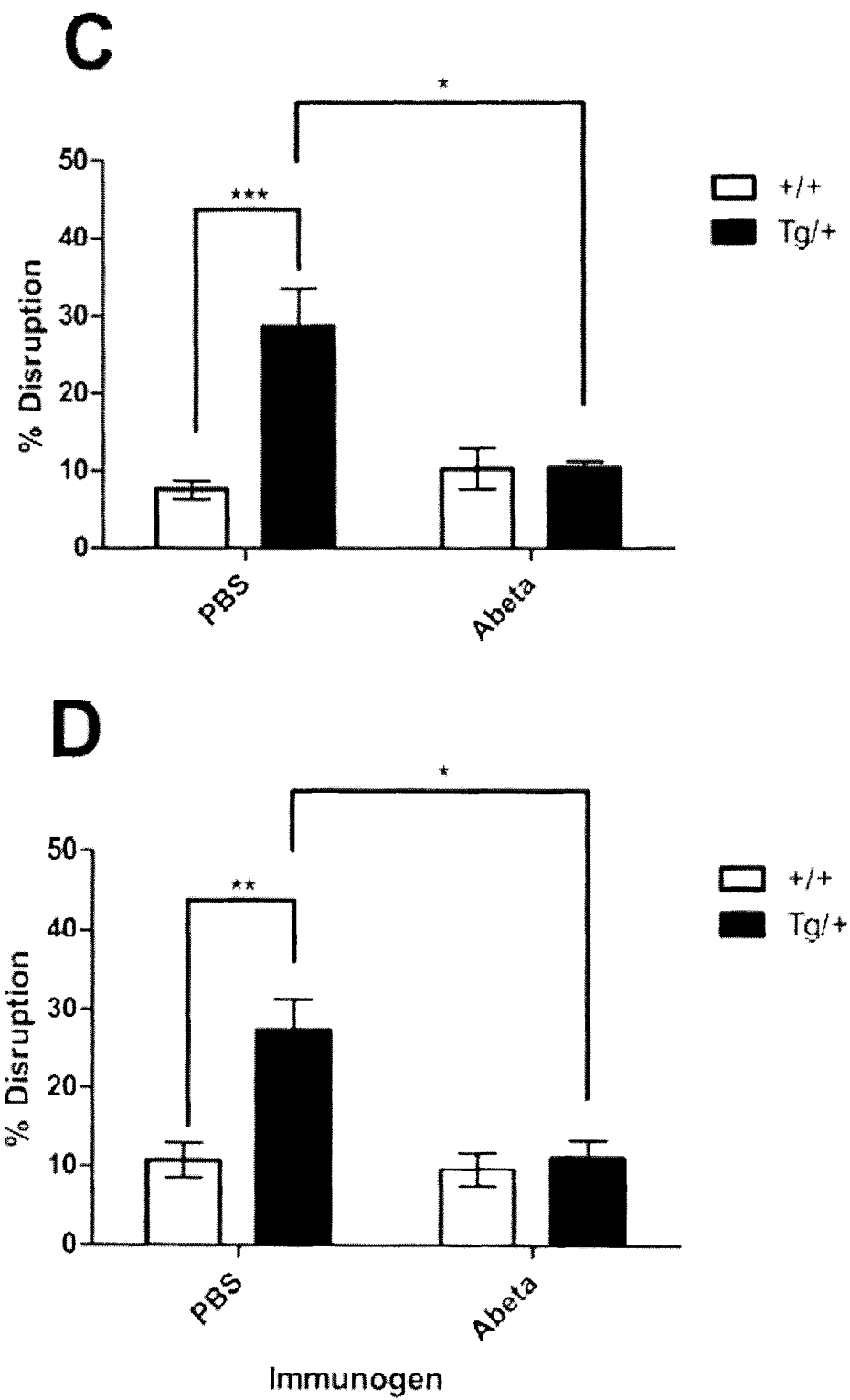

Quantitative Assessment of Cerebrovascular Tight Junction Pathology in Immunized Mice:

The incidence of TJ pathology was quantified by scoring the percentage of cerebral blood vessels with intact versus perforated TJs. Tg/+ mice immunized with PBS, both preventatively and therapeutically, had a significantly higher percentage of disrupted TJ expression compared to +/+, immunized with PBS, in the neocortex and the hippocampus (FIG. 12). Consistent with our previous data demonstrating the benefit of Aβ immunization on BBB pathology (Dickstein et al., FASEB J. 20, 426-433 (2006)), we show that Tg/+ mice immunized preventatively beginning at 6 weeks of age with Aβ displayed a significantly lower percentage of abnormal vascular TJ expression (averaging 10%; * p<0.05, 2-way ANOVA) compared to their PBS transgenic counterpart in the neocortex and hippocampus (FIGS. 12a and b). The level of TJ disruption in these mice was similar to +/+ controls injected with both Aβ and PBS. TJ pathology in Tg/+ mice immunized therapeutically with Aβ at 11 months of age exhibited a significant decrease (averaging 10%; * p<0.05, 2-way ANOVA) in TJ pathology compared to Tg/+ mice immunized with PBS in both the neocortex and hippocampus (FIGS. 12c and d). Moreover, immunization with Aβ after disease onset was able to restore TJ protein expression to levels similar to +/+ (FIGS. 12c and d). It is important to note that PBS or Aβ treated+/+ mice resulted in minimal TJ disruption.

Figure 13:
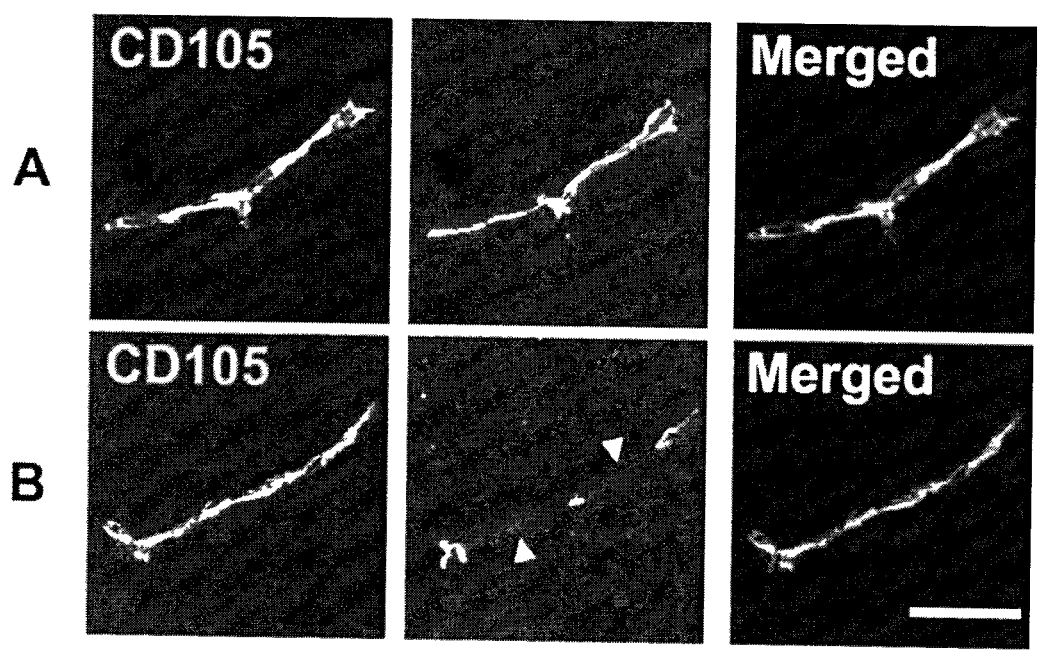
FIG. 13: Aβ immunized Tg2576 mice have reduced microvascular density. Representative images of ubiquitous CD105 (green) cerebrovasculature staining regardless of the (a) absence or (b) presence (white arrowheads) of ZO-1 (red) abnormalities. Scale bar represents 20 μm. A significantly increased MVD was seen in Tg/+, PBS compared to Tg/+, Aβ and +/+, PBS immunized mice. These findings were consistent between the (c) preventative (n=4 for all groups) and (d) therapeutic (+/+, PBS, n=4; Tg/+, PBS, n=3; +/+, Aβ, n=4; Tg/+, Aβ, n=4) immunization strategies. The average brain to body weight ratio in mice immunized either (e) preventatively (+/+, PBS, n=5; Tg/+, PBS, n=4; +/+, n=5; Tg/+, Aβ, n=3) or (f) therapeutically (+/+, PBS, n=4; Tg/+, PBS, n=4; +/+, n=5; Tg/+, n=5) did not reach significance. * p<0.05, *** p<0.001.

Angiogenesis in Immunized Tg2576 Brains:

The microvascular density (MVD) is increased in aged Tg2576 AD model mice (Biron et al., PLoS ONE 6, e23789 (2011)) suggesting an increase in angiogenesis with disease progression and severity. Does active Aβ immunization alter the density of vessels in AD mice? MVD was quantified by CD105, a known angiogenic endothelial marker, immunofluorescence staining patterns in the neocortex and hippocampus. CD105 staining was ubiquitous in the cerebrovasculature regardless of the absence (FIG. 13a) or presence (FIG. 13b) of TJ abnormalities. Tg/+ mice preventatively immunized with PBS had over double the MVD (0.4560±0.0072; *** p<0.001, 2-way ANOVA) compared to its PBS+/+ (0.1951±0.0130) (FIG. 13c). In contrast, the MVD in Tg/+ mice preventatively immunized with Aβ was significantly reduced compared to its PBS control of the same genotype (0.1972±0.0075; * p<0.05, 2-way ANOVA) (FIG. 13c) and at a similar level observed in +/+ animals. The MVD in the therapeutically treated mice mirrored the observations in the mice immunized preventatively. Tg/+ mice immunized after disease onset with PBS (0.4939±0.0077) had over double the MVD compared to its PBS+/+ (0.2044±0.0222; *** p<0.001, 2-way ANOVA) (FIG. 13d). As seen in the Tg/+ mice immunized prior to disease onset, Tg/+ mice immunized with Aβ after disease onset also had a significantly reduced MVD (0.2180±0.0130; * p<0.05, 2-way ANOVA) compared to Tg/+ mice immunized with PBS (FIG. 13d). Changes in vascular density appeared to be independent of the physical size of the mice brain. The average brain to body weight ratio was not significant regardless of the genotype, immunogen or immunization strategy (FIGS. 13e and f).

Figure 14:
FIG. 14: Aβ deposition in immunized Tg2576 mice is altered. Representative images showing a general reduction of Aβ deposits (green) in (b and d) Tg/+, Aβ compared to (a and c) Tg/+, PBS mice immunized either (a an b) therapeutically or (c and d) preventatively.

Abeta Deposition in Immunized Tg2576 Brains:

As described previously (Dickstein et al., *FASEB J* 20, 426-433 (2006)), Tg/+ mice immunized with Aβ had a dramatic reduction in parenchymal Aβ plaques (FIG. 14a-d). A complete elimination in Aβ plaques was seen in the Tg/+ mice preventatively immunized with AP (FIG. 14d). However, therapeutically treated Tg/+ with Aβ had a dramatic decrease in Aβ plaque pathology (FIG. 14b).

Discussion

Aβ immunotherapy continues to be explored as an experimental treatment option for AD. The unexpected negative vascular side effects seen in the early clinical trials of the human AD vaccine demonstrates our limited knowledge of Aβ and AD pathogenesis. Existing models do not incorporate tenants that can explain these observations. This study demonstrated that in an active Aβ immunization AD mouse model BBB TJ integrity is related to angiogenesis driven by amyloidogenesis. Removing Aβ from the brain parenchyma eliminates the microvascular related TJ pathology. Furthermore, the observed CAA related microhemorrhaging in the human immunization trials might be explained by the loss of the TJs in the affected blood vessels.

BBB dysfunction was initially identified in animal models of AD (Ujiie et al., Microcirculation 10, 463-470 (2003)) and was later confirmed as a prominent, though unexplained, clinical feature of AD in patients (Farrall & Wardlaw, Neurobiol Aging 30, 337-352 (2009)). We recently proposed a new hypothesis that is consistent with the body of data relating to the BBB in AD: amyloidogenesis promotes extensive neoangiogenesis leading to increased vascular permeability and subsequent hypervascularization in AD (Biron et al., PLoS ONE 6, e23789 (2011)). Here we demonstrate that Aβ immunization modulates angiogenic signals in treated Tg2576 mice that overexpress the human APP695 containing the double missense Swedish mutations (K670N/M671L), which causes early-onset AD. The relative amount of angiogenesis can be quantified through the average microvascular staining densities of CD105 in the brain (Holley et al. Neurosci Lett 470, 65-70 (2010); Barresi et al., Acta Neuropathol 114, 147-156 (2007)). PBS treated Tg2576 mice, both preventatively and therapeutically, had significantly higher vascular densities compared to wild-type mice and Aβ treated Tg2576 mice. The changes in vascular density appeared to be independent of the physical size of the mouse brain. This implies that angiogenic signals are reduced when Aβ is removed. It is presumed that neuroinflammation is reduced as a result of amyloid immunotherapy. A reduction in both neuroinflammation and Aβ may directly or indirectly reduce angiogenic signals associated with both (Boscolo et al., Int J Mol Med 19, 581-587 (2007)).

A side effect observed in the failed clinical Aβ immunization trial was increased CAA-associated cerebral microhemorrhaging (Boche et al., Brain 131, 3299-3310 (2008)), also noted in a variety of AD mouse models after active (Wilcock et al., Neuroscience 144, 950-960 (2007); Petrushina et al., J Neuroinflammation 5, 42 (2008); Wilcock et al., *J Neurosci* 29, 7957-7965 (2009)) and passive (Pfeifer et al., Science 298, 1379, (2002); Racke, M. M. et al., J Neurosci 25, 629-636 (2005); Wilcock, D. M. et al., J Neuroinflammation 1, 24 (2004)) immunization. Disruption of the cerebrovasculature TJs by angiogenesis does explain this side effect. The following Aβ removal model is proposed. Pre-immunization, the abundance of Aβ influences the integrity of the BBB endothelia through triggered neoangiogenesis resulting in the disruption of the TJs. Microvascular leakage ensues allowing peripheral amyloid to enter the brain and coalesce as neurotoxic amyloid plaques. Cerebrovascular damage is further exasperated by and Aβ induced ROS derived from NADPH-oxidase (Park, L. et al., J Neurosci 25, 1769-1777 (2005)). Microhemorrhages result from TJ weakening as a result of angiogenesis leading to hypervascularity. During immunization, various Aβ clearance mechanisms are activated including opsonization, microglia removal and antibody disaggregation. As Aβ plaques are dissolved, solubilized Aβ is removed from the brain parenchyma along perivascular drainage routes (Weller et al., Alzheimers Res Ther 1, 6 (2009)). Immunization therefore, neutralizes the pro-angiogenic signal by stimulating an immune response to Aβ but other aspects of the disease, once formed, may be unresolved by immunization. For reasons that are yet known, the perivascular drainage of Aβ is halted, possibly by BBB resealing and becomes deposited in the cerebral arteries, resulting in CAA. It should be noted that the primary Aβ species found deposited in the CAA-affected vasculature is the more soluble $A\beta_{1-40}$, believed to be of neuronal origin (Herzig et al., Brain Pathol 16, 40-54 (2006)). This model appears to be parallel to the failed human AD Aβ immunization trial (Boche et al., Brain 131, 3299-3310 (2008)).

Our objective was to determine if immunization with Aβ peptides can resolve amyloidogenesis triggered angiogenesis and hypervascularity in Tg2576 AD mouse. We find reversion of hypervascularization follows immunization with Aβ. This appears to be the first example of vascular reversion where vascular density reverts to normal levels following therapeutic intervention. These data also imply the existence of greater vascular plasticity than has been previously reported. We could envision halting angiogenesis without resolving vascular density so this may imply that the amyloidogenic signal is required to maintain hypervascularity. Once the signal is removed, hypervascularity subsides. These data clearly underlie a vascular angiogenesis model of AD pathophysiology and provide the first evidence that modulating angiogenesis, repairs damage in the AD brain. Recently, the anti-proliferative drug, bexarotene, an oral anticancer agent, has been shown to reduce plaque burden and increase memory performance in animal models of AD (http://www.sciencemag.org/content/early/2012/02/08/science.1217697). This study interprets bexarotene acting on retinoid X receptors to affect APOE transport thereby reducing plaque accumulation or turnover, but other modes of action in AD are possible. Bexarotene (Targretin) is also known to increase apoptosis and alters cell cycle control, differentiation, anti-metastatic activity, and finally, anti-angiogenic activity (www.ncbi.nlm.nih.gov/pmc/articles/PMC3120806/). It inhibits angiogenesis by suppressing the proliferation, adhesion, invasion and migration of endothelial cells directly, and affected the expression of VEGF (www.ncbi.nlm.nih.gov/pmc/articles/PMC3120806/). These data and those presented herein, therefore directly point towards reversing cerebrovasculature angiogenesis as a new therapeutic modality for AD.

The disclosure of all patents, publications, including published patent applications, and database entries referenced in this specification are expressly incorporated by reference in their entirety to the same extent as if each such individual patent, publication, and database entry were expressly and individually indicated to be incorporated by reference.

Although the invention has been described with reference to certain specific embodiments, various modifications thereof will be apparent to those skilled in the art without departing from the spirit and scope of the invention. All such modifications as would be apparent to one skilled in the art are intended to be included within the scope of the following claims.

We claim:

1. A method of maintaining and/or restoring tight junction integrity in cerebral vessels and thereby ameliorating symptoms of Alzheimer's Disease in a subject having Alzheimer's Disease consisting of administering to the subject bevacizumab.

2. The method of claim 1, wherein blood-brain barrier integrity is maintained and/or restored.

3. The method according to claim 1, wherein there is vascular reversion.

4. A method of maintaining and/or restoring blood-brain barrier (BBB) integrity in a patient having Alzheimer's disease and thereby treating Alzheimer's disease, consisting of administering to the subject bevacizumab.

5. The method according to claim 4, wherein there is vascular reversion.

* * * * *

UNITED STATES PATENT AND TRADEMARK OFFICE
CERTIFICATE OF CORRECTION

PATENT NO. : 10,792,347 B2
APPLICATION NO. : 15/496106
DATED : October 6, 2020
INVENTOR(S) : Wildred Jefferies et al.

Page 1 of 1

It is certified that error appears in the above-identified patent and that said Letters Patent is hereby corrected as shown below:

In the Specification

Column 5, Lines 45-46, "(+/+) mice was quantified by CD105 staining (a) Preventatively immunized" should be --(+/+) mice was quantified by CD105 staining. (a) Preventatively immunized--.

Column 8, Line 21, "D(LPR) or" should be --$_D$(LPR) or--.

Column 15, Lines 64-65, "10% SDS-PAGE gels according to standard practices Immunoblotting was performed" should be --10% SDS-PAGE gels according to standard practices. Immunoblotting was performed--.

Column 18, Line 6, "of AD into clinical disease in humans In the cortex of the AD" should be --of AD into clinical disease in humans. In the cortex of the AD--.

Signed and Sealed this
First Day of December, 2020

Andrei Iancu
*Director of the United States Patent and Trademark Office*